(12) United States Patent
Fortte et al.

(10) Patent No.: US 8,759,554 B2
(45) Date of Patent: Jun. 24, 2014

(54) MATERIALS FOR ELECTRONIC DEVICES

(75) Inventors: Rocco Fortte, Frankfurt am Main (DE); Amir Hossain Parham, Frankfurt am Main (DE); Teresa Mujica-Fernaud, Darmstadt (DE)

(73) Assignee: Merck Patent GmbH (DE)

( * ) Notice: Subject to any disclaimer, the term of this patent is extended or adjusted under 35 U.S.C. 154(b) by 221 days.

(21) Appl. No.: 13/384,273

(22) PCT Filed: Jun. 17, 2010

(86) PCT No.: PCT/EP2010/003660
§ 371 (c)(1),
(2), (4) Date: Mar. 27, 2012

(87) PCT Pub. No.: WO2011/006568
PCT Pub. Date: Jan. 20, 2011

(65) Prior Publication Data
US 2012/0172597 A1    Jul. 5, 2012

(30) Foreign Application Priority Data
Jul. 16, 2009  (DE) .......................... 10 2009 033 371

(51) Int. Cl.
*C07C 13/64* (2006.01)
*H01L 51/54* (2006.01)

(52) U.S. Cl.
USPC .......................................... 552/284; 313/498

(58) Field of Classification Search
USPC ............................ 552/284; 313/498; 528/396
See application file for complete search history.

(56) References Cited

U.S. PATENT DOCUMENTS

2011/0112275 A1 * 5/2011 Parham et al. ................. 528/396

FOREIGN PATENT DOCUMENTS

| EP | 2075309 A2 | 7/2009 |
| JP | 10340785 A | 12/1998 |
| JP | 2008231052 A | 10/2008 |

OTHER PUBLICATIONS

Grisorio, et al., "Synthesis of Bifluorene-Based Molecular Materials: Effect of C-9 Spirocyclohexane Functionalization and End-Group Tailoring", Tetrahedron, vol. 64, (2008), pp. 8738-8745.
Grisorlo, et al., "Influencing the Spectral Stability and the Electroluminescence Behavior of New Blue-Emitting Bifluorene-Based Materials by the 7,7'-Functionalization of the Core", J. Phys. Chem. C., vol. 112, (2008), pp. 7005-7014.
Yuan, et al., "Star-Shaped Ollgo(Fluorene Ethynylene)-Functionalized Truxene Derivatives: Synthesis, Characterization, and Their Size Effects", Tetrahedron, vol. 65, (2009), pp. 4165-4172.

* cited by examiner

*Primary Examiner* — Charanjit Aulakh
(74) *Attorney, Agent, or Firm* — Drinker Biddle & Reath LLP

(57) ABSTRACT

Compounds containing arylalkynyl groups with multiple ring bridging, the use of those compounds in electronic devices, and electronic devices containing the compounds.

11 Claims, No Drawings

MATERIALS FOR ELECTRONIC DEVICES

RELATED APPLICATIONS

This application is a national stage application (under 35 U.S.C. §371) of PCT/EP2010/003660, filed Jun. 17, 2010, which claims benefit of German Application No. 10 2009 033 371.1, filed Jul. 16, 2009.

The present invention relates to compounds containing arylalkynyl groups with multiple ring bridging. The invention furthermore relates to the use of the compounds according to the invention in electronic devices, preferably organic electroluminescent devices, and to a process for the preparation of the compounds according to the invention. The invention furthermore relates to electronic devices comprising the compounds according to the invention.

Organic semiconductors, such as the compounds according to the invention disclosed below, are being developed for a series of different applications in the electronics industry. The compounds are used in electronic devices, preferably organic electroluminescent devices (OLEDs). The structure of these devices in which organic semiconductors are employed as functional materials is described, for example, in U.S. Pat. No. 4,539,507, U.S. Pat. No. 5,151,629, EP 0676461 and WO 98/27136.

There is a continuous demand for novel materials for use in electronic devices, in particular with respect to an improvement of the devices in the following aspects:
1. For a reduction in the operating voltage of the electronic devices, compounds having suitable HOMO or LUMO positions and thus easier electron injection are required.
2. There is still a need for improvement in the lifetime of the electronic devices in order to employ them for high-quality applications with a long life, in particular for blue-emitting devices.
3. There is likewise a need for improvement with respect to the thermal stability of the compounds used in the electronic devices. High thermal stability is necessary both during purification of the material by mass sublimation and also during application of the material by thermal evaporation. A high glass-transition temperature is also desirable for use of the compounds in heat-stable electronic devices with a long life.
4. The efficiency of organic electroluminescent devices should be increased further, in particular with respect to high-quality applications.

JP 2005174735 describes a multiplicity of compounds which can be summarised under the general structural formula Ar—C≡C—Ar as functional materials in organic electroluminescent devices. However, there continues to be a demand for alternative materials, in particular materials having improved properties with respect to one or more of the aspects mentioned above.

In accordance with the prior art, use is made, in particular, of condensed aromatic compounds, in particular anthracene or pyrene derivatives, as matrix materials for fluorescent OLEDs, especially for blue-emitting electroluminescent devices, for example 9,10-bis-(2-naphthyl)anthracene (U.S. Pat. No. 5,935,721). Further anthracene derivatives are disclosed in WO 01/076323, in WO 01/021729, in WO 04/013073, in WO 04/018588, in WO 03/087023 or in WO 04/018587. Matrix materials based on aryl-substituted pyrenes and chrysenes are disclosed in WO 04/016575. For high-quality applications, it is desirable to have available further matrix materials, preferably those which effect improvements in one or more of the aspects mentioned above.

Prior art which may be mentioned in the case of blue-emitting compounds is the use of arylvinylamines (for example WO 04/013073, WO 04/016575, WO 04/018587). There is a need for improvement in the case of these compounds, in particular with respect to the thermal stability and the achievement of the desired deep-blue colour coordinates.

In electronic devices in accordance with the prior art, the electron-transport compound used in organic electroluminescent devices is $AlQ_3$ (aluminium trishydroxyquinolinate) (U.S. Pat. No. 4,539,507).

Here too, there is a continuous demand for alternative materials having electron-transport properties which preferably have high thermal stability, good synthetic accessibility and low hygroscopicity and furthermore preferably effect high charge-carrier mobility.

In summary, there is a demand for alternative compounds for use in electronic devices, in particular matrix materials for fluorescent dopants and phosphorescent dopants, but also for dopants, in particular blue-emitting dopants, and hole-transport materials and electron-transport materials, which preferably have one or more of the following advantageous properties: high thermal stability, improvement in efficiency and improvement in the lifetime of the devices comprising the alternative compounds, high reproducibility of the performance profile of the devices, and good synthetic accessibility.

The object on which the present invention is based thus consists in the provision of improved compounds of this type for use in electronic devices, preferably organic electroluminescent devices.

It has now been found that multiply bridged arylalkyne derivatives of the general formula (I) are very highly suitable for use as functional materials in organic electroluminescent devices.

The present invention thus relates to compounds of the formula (I), formula (I)

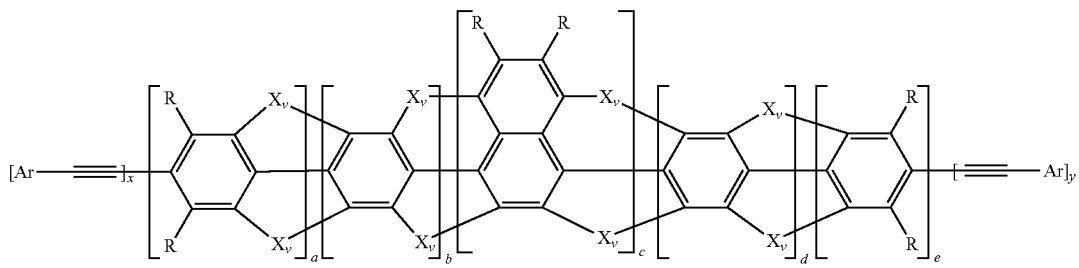

where the following applies to the symbols and indices used:

X is on each occurrence, identically or differently, $C(R)_2$, $Si(R)_2$, NR, C=O, C=S, C=NR, COO, CONR, O, S, SO, $SO_2$, P(=O)R or $C(=CR_2)$;

Ar is on each occurrence, identically or differently, an aromatic or heteroaromatic ring system having 5 to 60 aromatic ring atoms, which may in each case be substituted by one or more radicals R;

v is, independently of one another, 0 or 1, with the proviso that the sum of the values of the indices v is at least equal to two, i.e. at least two units X are present, and the additional proviso that at least one aromatic ring is present which is substituted by at least two units X; v=0 here means that the corresponding group X is not present and instead a substituent R is bonded at the positions in question, where v=0 basically applies if no adjacent aromatic ring is present for bridging in the respective position;

a,e are, independently of one another, identically or differently, 0 or 1, b,c,d are, independently of one another, identically or differently, 0, 1 or 2, x, y are, independently of one another, identically or differently, 0 or 1, with the proviso that x+y≥1;

and, for the sum of a, b, c, d and e: a+b+c+d+e≥2;

and all free bonding sites may optionally be substituted by R, where R is defined as follows:

R is on each occurrence, identically or differently, H, D, F, Cl, Br, I, $N(R^1)_2$, CN, $NO_2$, $Si(R^1)_3$, $B(OR^1)_2$, C(=O)$R^1$, $P(=O)(R^1)_2$, $S(=O)R^1$, $S(=O)_2R^1$, $OSO_2R^1$, a straight-chain alkyl, alkoxy or thioalkoxy group having 1 to 40 C atoms or an alkenyl group having 2 to 40 C atoms or a branched or cyclic alkyl, alkoxy or thioalkoxy group having 3 to 40 C atoms, where the said groups may each be substituted by one or more radicals $R^1$ and where one or more adjacent or non-adjacent $CH_2$ groups may be replaced by $R^1C=CR^1$, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S, COO or $CONR^1$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may be substituted by one or more radicals $R^1$, or an aralkyl or heteroaralkyl group having 5 to 60 aromatic ring atoms, which may in each case be substituted by one or more radicals $R^1$; two or more substituents R on the phenylene groups and/or on the naphthylene groups and/or on the substituents Ar here may be linked to one another and optionally form a mono- or polycyclic aliphatic or aromatic ring system;

$R^1$ is on each occurrence, identically or differently, H, D, F, Cl, Br, I, CN or an aliphatic, aromatic or heteroaromatic organic radical having 1 to 40 C atoms, in which, in addition, one or more H atoms may be replaced by D, F, Cl, Br, I, CN, $OR^2$, $SR^2$ or $N(R^2)_2$, where one or more adjacent or non-adjacent $CH_2$ groups may be replaced by $R^2C=CR^2$, COO or $CONR^2$; two or more adjacent or non-adjacent radicals $R^1$ here may be linked to one another and optionally form a mono- or polycyclic, aliphatic or aromatic ring system;

$R^2$ is on each occurrence, identically or differently, H, D or an aliphatic, aromatic or heteroaromatic organic radical having 1 to 20 C atoms, in which, in addition, one or more H atoms may be replaced by D or F; two or more adjacent or non-adjacent radicals $R^2$ here may be linked to one another and optionally form a mono- or polycyclic aliphatic or aromatic ring system.

The radicals R preferably do not form polycyclic aromatic systems condensed onto the phenylene or naphthylene units by linking to one another, in particular do not form polycyclic condensed aromatic systems which have more than two aromatic nuclei, such as, for example, anthracene or pyrene.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, benzothiophene, benzofuran and indole, etc.

For the purposes of this invention, the radical Ar in accordance with the definition given above is particularly preferably selected from benzene, biphenyl, terphenyl, naphthalene, pyridine, pyrimidine, pyrazine, pyridazine, triazine, quinoline, isoquinoline, furan, thiophene, benzothiophene and indole, each of which may be substituted by one or more radicals R.

An aralkyl group in the sense of this invention is an alkyl group which is substituted by an aryl group, where the term aryl group is to be understood as defined above and alkyl group is defined as a non-aromatic organic radical having 1-40 C atoms, in which, in addition, individual H atoms or $CH_2$ groups may be substituted by the groups mentioned above in the definition of R and $R^1$.

A heteroaralkyl group in the sense of this invention is an alkyl group which is substituted by a heteroaryl group, where the term heteroaryl group is to be understood as defined above and alkyl group is defined as a non-aromatic organic radical having 1-40 C atoms, in which, in addition, individual H atoms or $CH_2$ groups may be substituted by the groups mentioned above in the definition of R and $R^1$.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via one or more single bonds are also taken to be aromatic or heteroaromatic ring systems in the sense of this invention.

For the purposes of the present invention, a $C_1$- to $C_{40}$-alkyl group, in which, in addition, individual H atoms or $CH_2$ groups may be substituted by the groups mentioned above in the definition of the groups R and $R^1$, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is preferably taken to mean methoxy, trifluoromethoxy, ethoxy, n-propoxy, i-propoxy, n-butoxy, butoxy, s-butoxy, t-butoxy or 2-methylbutoxy.

An aromatic or heteroaromatic ring system having 5-60 aromatic ring atoms, which may also in each case be substituted by the above-mentioned radicals R and which may be linked to the aromatic or heteroaromatic ring system via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydro-pyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred embodiment of the invention, the group X is selected, identically or differently on each occurrence, from $C(R)_2$, NR, O, S or C=O. The group X is particularly preferably, identically or differently on each occurrence, $C(R)_2$.

In a further preferred embodiment, the sum of the values of the indices v is 2, 3 or 4, i.e. two, three or four bridging groups X are present in the central structural unit of the molecule, and the sum of the values of the indices v is particularly preferably equal to two or three, very particularly preferably equal to two.

In a preferred embodiment of the invention, a+b+c+d+e is equal to 2, 3 or 4, particularly preferably 2 or 3.

It is furthermore preferred for the individual indices b, c and d to be, identically or differently, 0 or 1.

A preferred embodiment of the invention exists if c is equal to 1, i.e. a naphthyl group is present in the central structural unit of the molecule.

A further preferred embodiment of the invention exists if the sum of the values of the indices x and y is equal to 1.

In a further preferred embodiment, R stands for H, D, CN or a straight-chain alkyl group having 1 to 20 C atoms or an alkenyl group having 2 to 20 C atoms or a branched or cyclic alkyl group having 3 to 20 C atoms or an aromatic or heteroaromatic ring system having 5 to 40 aromatic ring atoms, where the said groups may each be substituted by one or more identical or different radicals $R^1$.

R particularly preferably stands for H, D, CN or a straight-chain alkyl group having 1 to 10 C atoms or an alkenyl group having 2 to 10 C atoms or a branched or cyclic alkyl group having 3 to 10 C atoms or an aryl or heteroaryl group having 5 to 20 aromatic ring atoms, where the said groups may each be substituted by one or more identical or different radicals $R^1$.

R very particularly preferably stands for H, D, CN, or an alkyl group having 1 to 10 C atoms, which may optionally be substituted by one or more identical or different radicals $R^1$.

Preferred embodiments of compounds of the general formula (I) are compounds of the formula (II), formula (II)

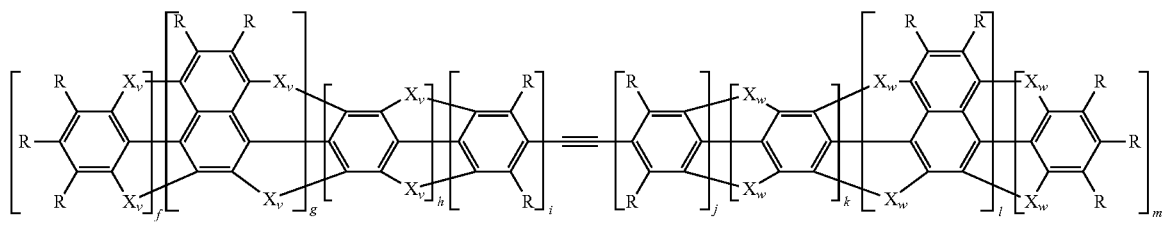

where the indices and symbols already occurring in formula (I) are defined as mentioned above, and it is furthermore stipulated that the indices g, h, k and l are, independently of one another, 0, 1 or 2, and the indices f, i, j and m are, independently of one another, 0 or 1, where the sum of the values of the indices f, g, h and i is greater than or equal to 2, and that w is on each occurrence, identically or differently, 0 or 1; v=0 or w=0 here means that the corresponding group X is not present and instead a substituent R is bonded at the positions in question, where v=0 or w=0 basically applies if no adjacent aromatic ring is present for bridging in the respective position.

Furthermore, the sum of the values of the indices v in the compounds of the formula (II) according to the invention must be at least equal to 2, where at least one aromatic ring which is substituted by at least two units X is present.

For compounds of the formula (II) according to the invention, the individual indices f, g, h, i, j, k, l and m are preferably, independently of one another, 0 or 1, and j+k+l+m is ≥1, and the sum of the values of the indices w is at least equal to 1, i.e. at least one unit X is present in the right-hand half of the molecule.

The following particularly preferably applies to the indices f, g, h, i, j, k, l and m:

$2 \leq f+g+h+i \leq 4$ and/or $2 \leq j+k+l+m \leq 4$.

For the group X, the embodiments explicitly mentioned above are furthermore preferred.

It is preferred for the sum of the values of the indices g and l to be equal to 1 or 2, very particularly preferably equal to 2.

Furthermore, for the compounds of the formula (II) according to the invention, the same embodiments are preferred which were also mentioned above as being preferred for compounds of the formula (I).

Preferred embodiments of compounds of the general formula (I) are furthermore compounds of the formula (III),

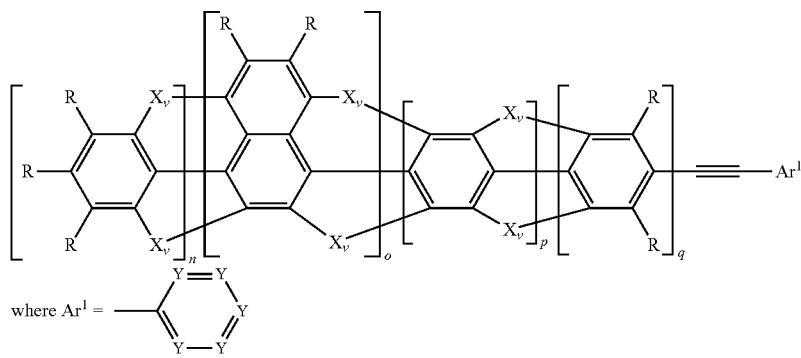

formula (III)

where the indices and symbols already occurring in formula (I) are as defined above, and it is furthermore stipulated that the indices n and q are, independently of one another, 0 or 1, that the indices o and p are, independently of one another, 0, 1 or 2, and that Y is on each occurrence, identically or differently, CR, N or P. In addition, the sum of the values of the indices v is greater than or equal to 2, and at least one aromatic ring which is substituted by at least two units X is present; v=0 here means that the corresponding group X is not present and instead a substituent R is bonded at the positions in question, where v=0 basically applies if no adjacent aromatic ring is present for bridging in the respective position. As an additional proviso, the sum of the indices n, o, p and q in formula (III) is at least equal to 2.

Y preferably stands for CR or N. Y furthermore preferably stands for CR or N and not more than two groups Y represent N alongside one another.

It is likewise preferred for the index o to have the value 1 or 2, particularly preferably the value 1.

Ar¹ preferably represents a phenyl, biphenyl, terphenyl, pyrazinyl, pyridazyl, pyrimidyl or triazinyl group, each of which may be substituted by one or more radicals R.

For the compounds of the formula (III) according to the invention, the same embodiments are preferred which were also mentioned above as being preferred for compounds of the formula (I) or (II).

Preferred embodiments of the compounds according to the invention are, in addition, compounds which fall under the structural formulae (IV) to (XII),

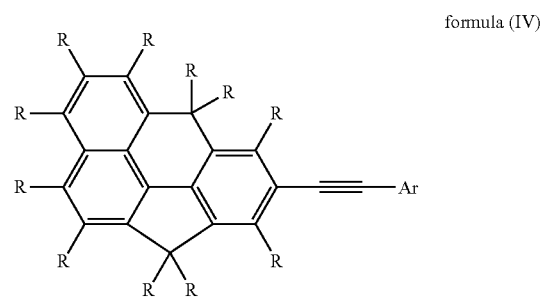

formula (IV)

-continued

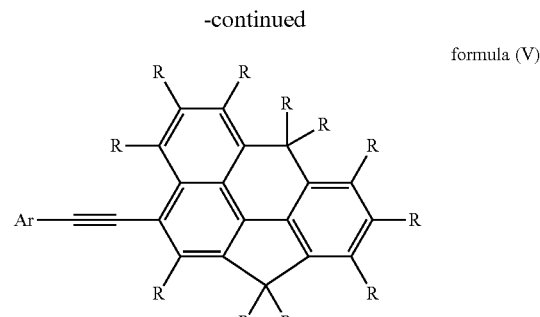

formula (V)

formula (VI)

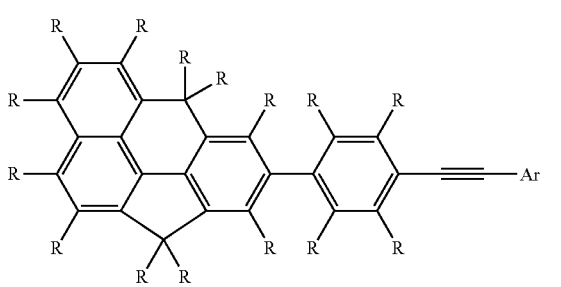

formula (VII)

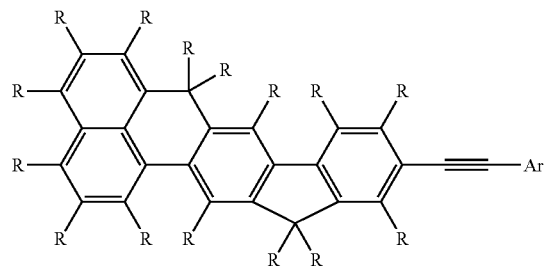

formula (VIII)

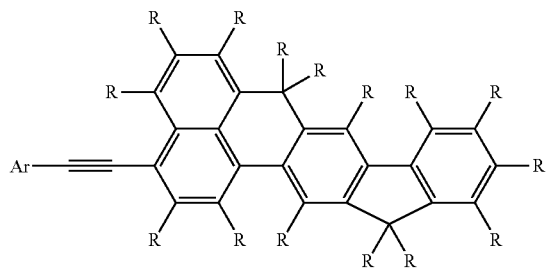

formula (IX)

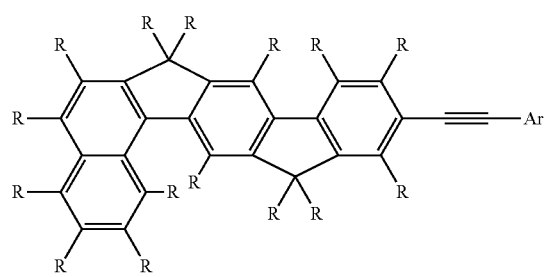

formula (X)

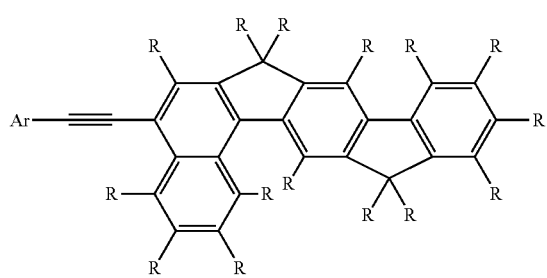

formula (XI)

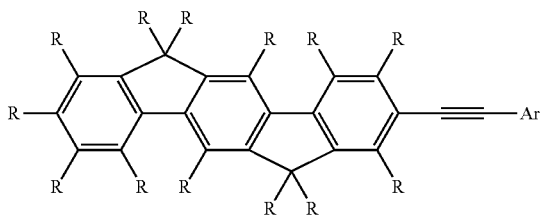

formula (XII)

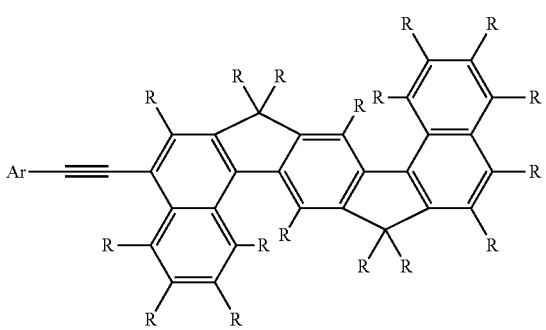

where Ar and R are as defined above.

The preferred embodiments for R that are mentioned above also apply to compounds of one of the formulae (IV) to (XII).

For the purposes of this invention, the radical Ar in compounds of the formulae (IV) to (XII) in accordance with the above-mentioned definition is particularly preferably selected from benzene, biphenyl, terphenyl, naphthalene, pyridine, pyrimidine, pyrazine, pyridazine, triazine, quinoline, isoquinoline, thiophene, benzothiophene and indole, each of which may be substituted by one or more radicals R.

In the compounds according to the invention, it is generally preferred for one or more polymerisable functional groups or one or more electron-withdrawing or electron-donating groups to be present.

Examples of compounds according to the invention are shown below:

(1)

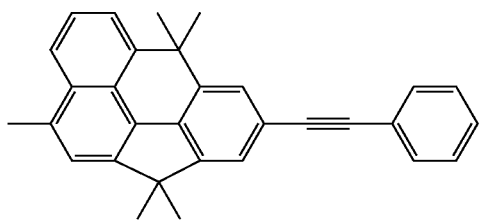

(2)

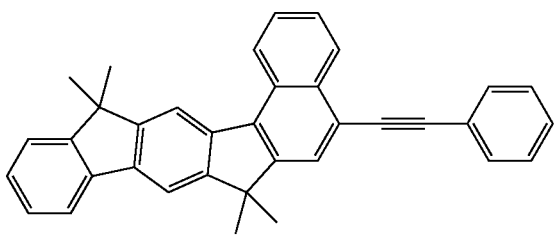

-continued
(3)
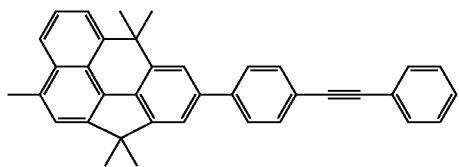
(4)
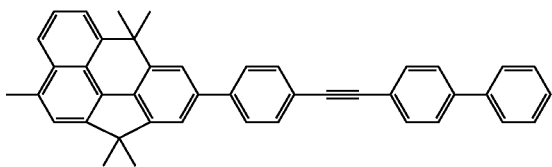
(5)
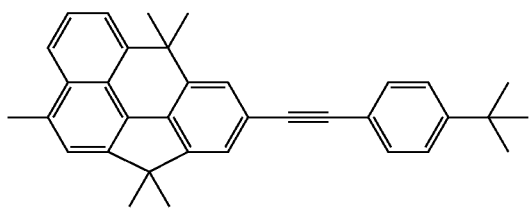
(6)
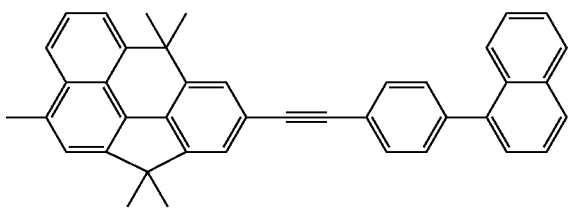
(7)
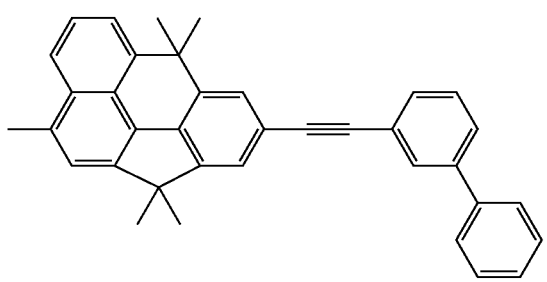
(8)
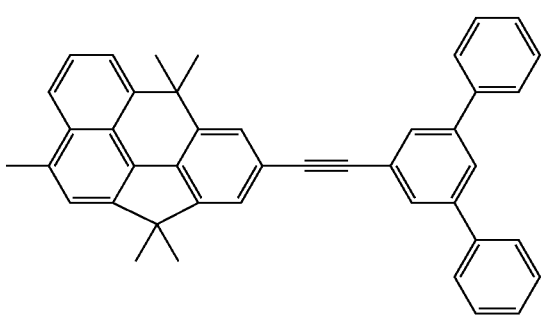
(9)
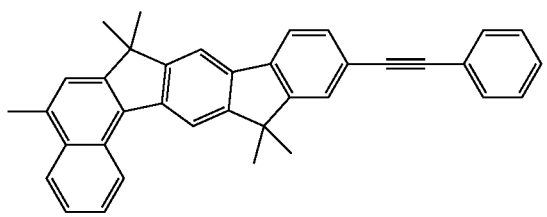
(10)
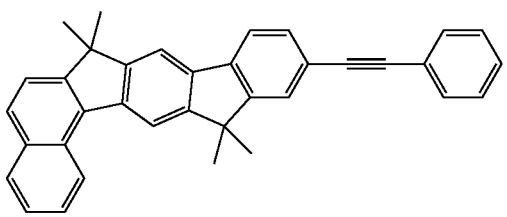
(11)
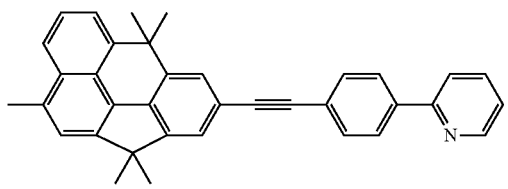
(12)
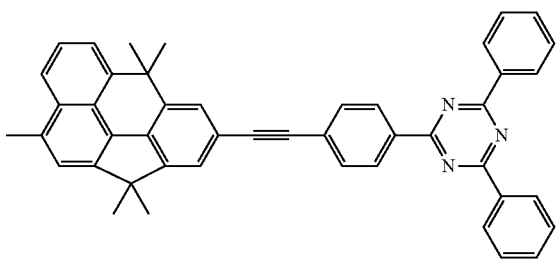
(13)
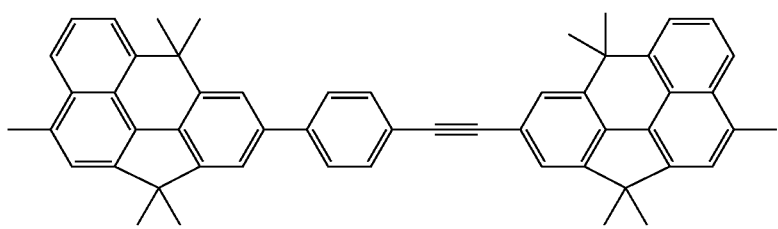

-continued
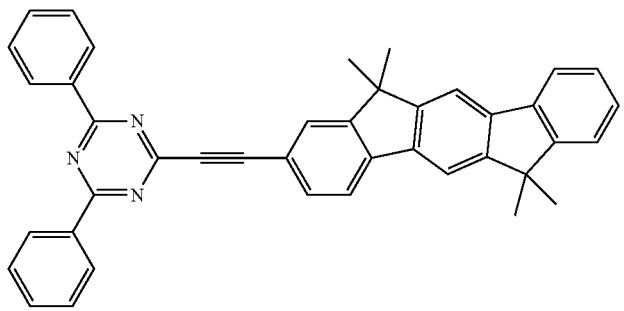
(14)
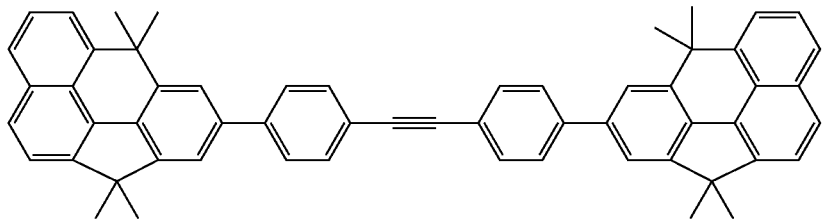
(15)
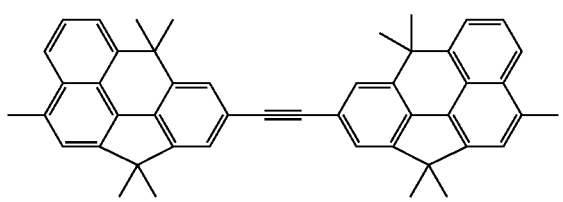
(16)
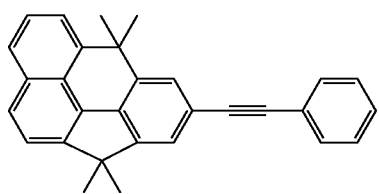
(17)
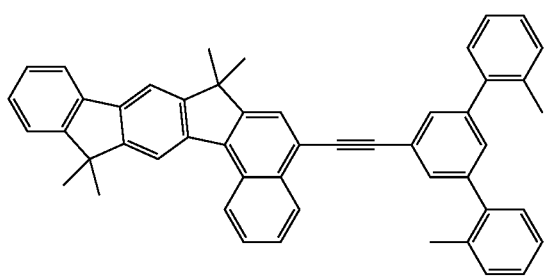
(18)
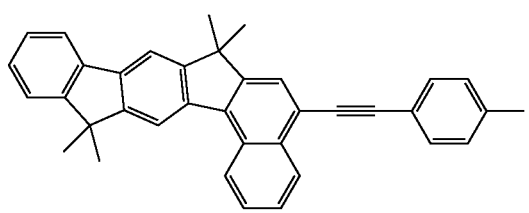
(19)
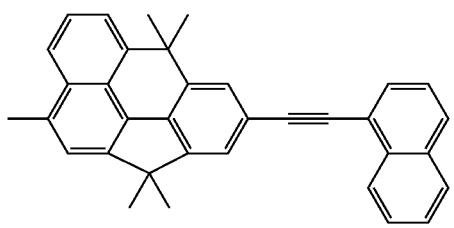
(20)
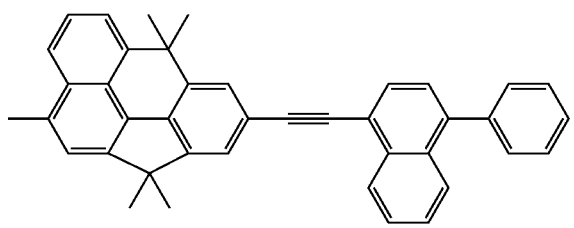
(21)
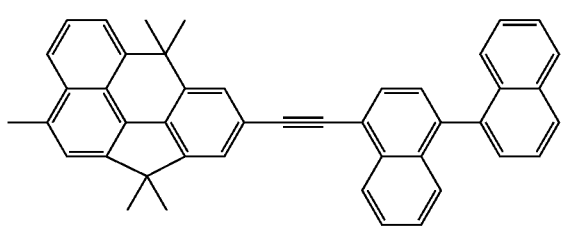
(22)
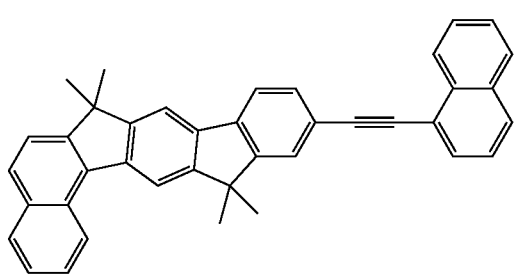
(23)

-continued
(24)
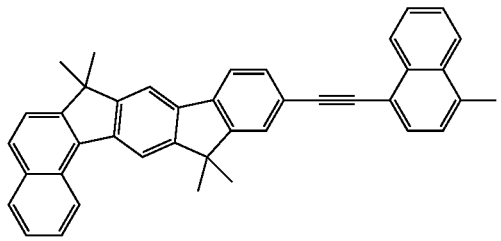
(25)
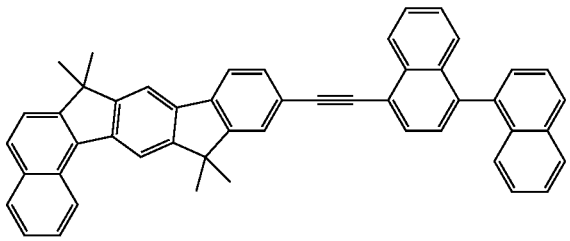
(26)
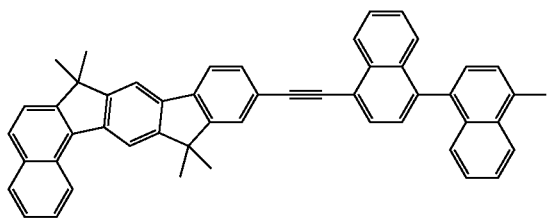
(27)
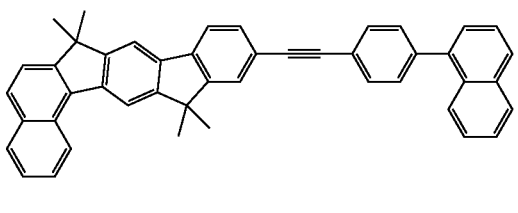
(28)
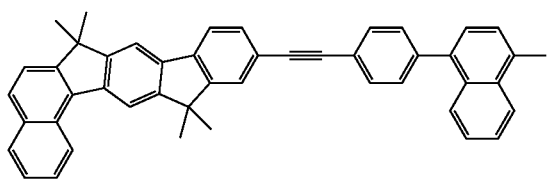
(29)
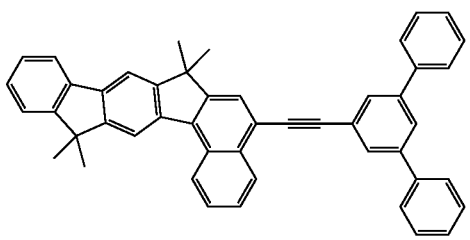
(30)
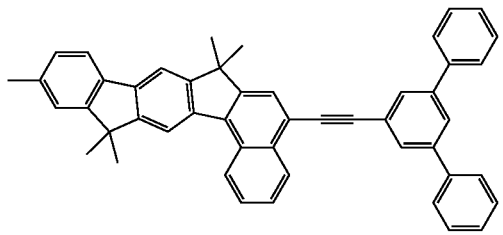
(31)
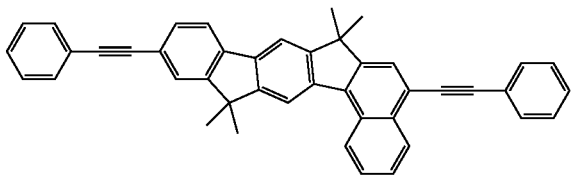
(32)
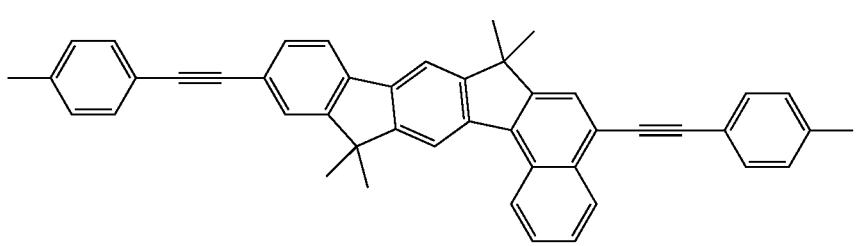
(33)
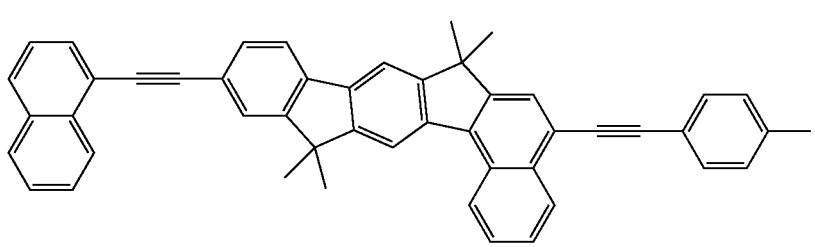

-continued
(34)
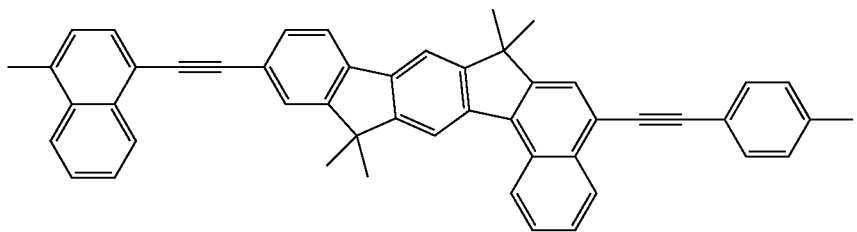
(35)
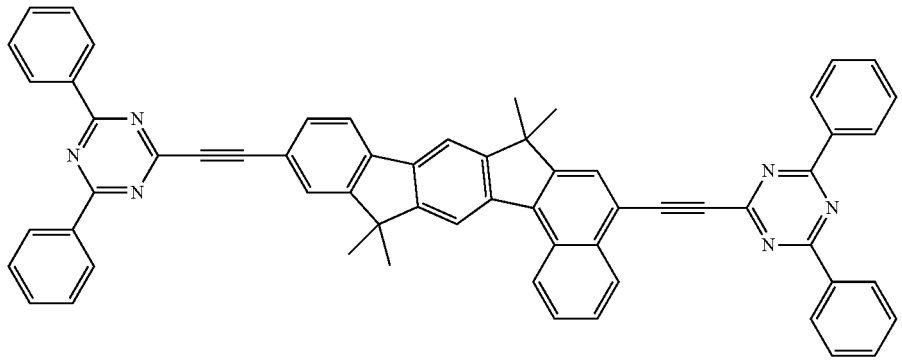
(36)
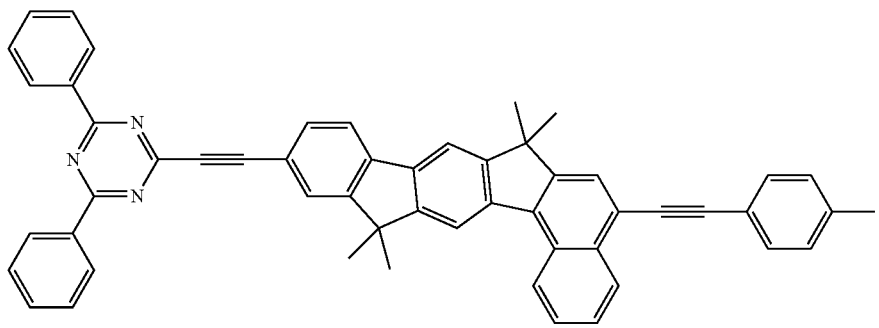
(37)
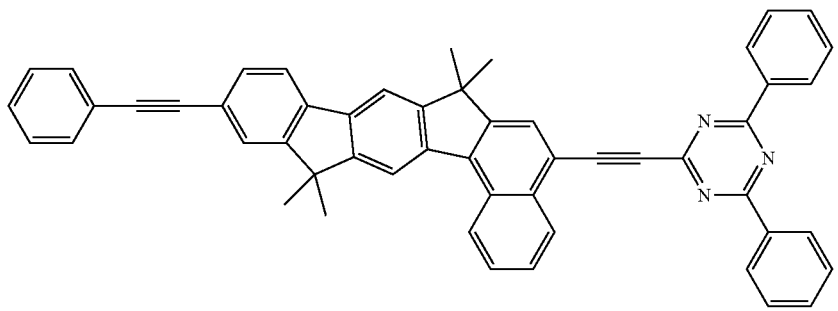
(38) (39)
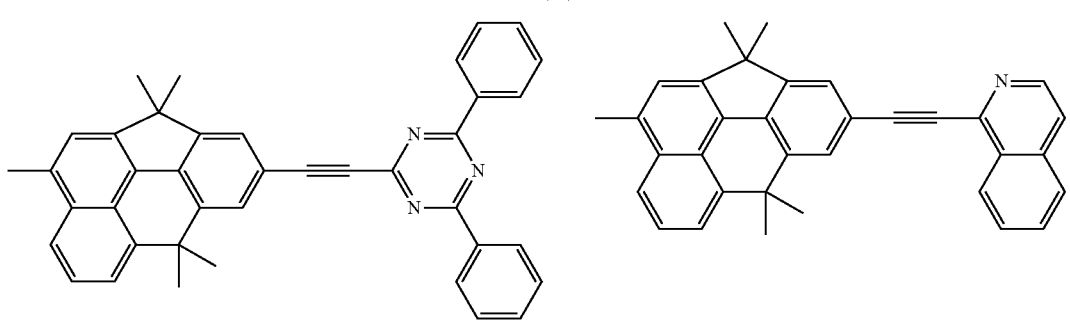

-continued
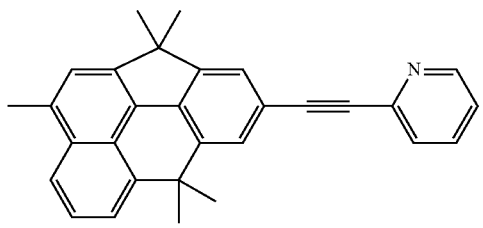
(40)
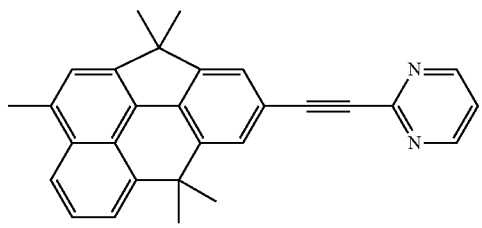
(41)
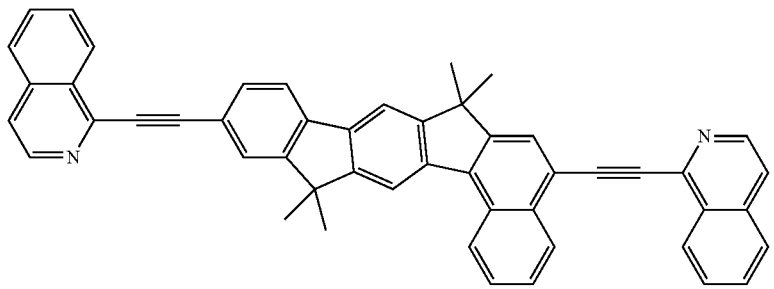
(42)
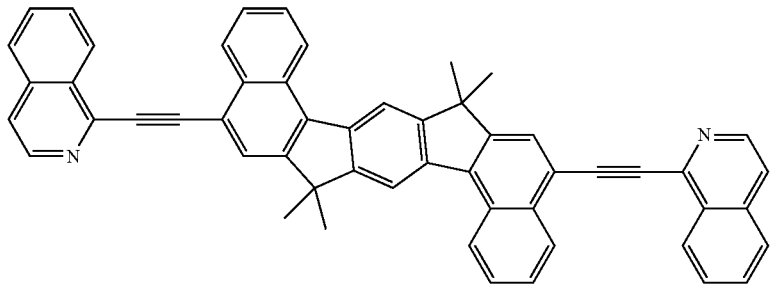
(43)
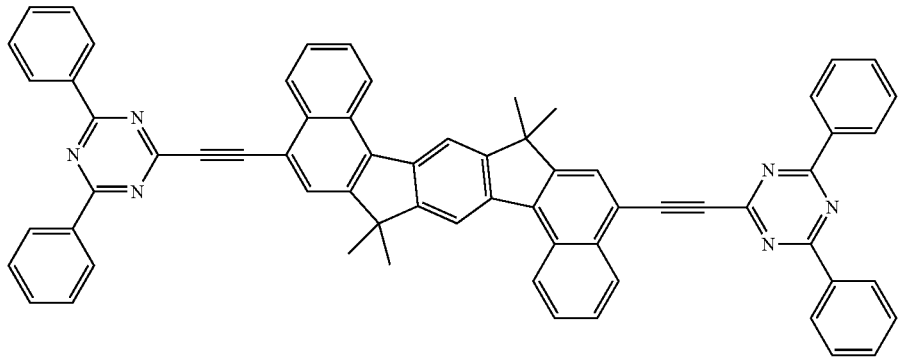
(44)
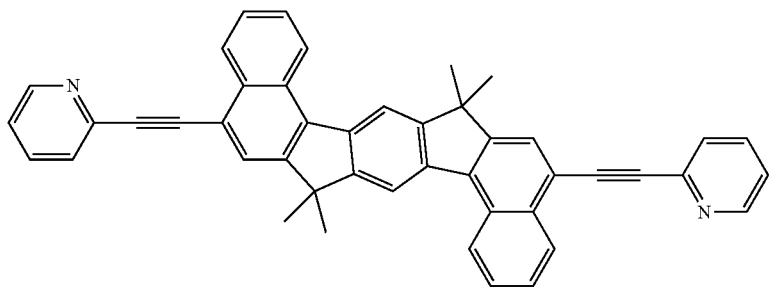
(45)

-continued

(46)
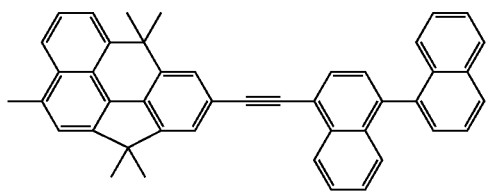

(47)
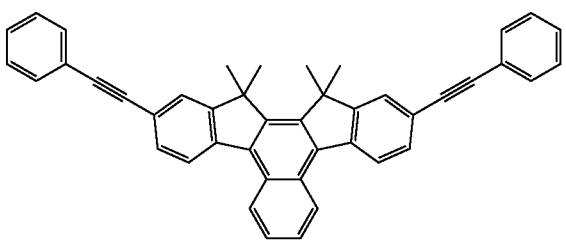

(48)
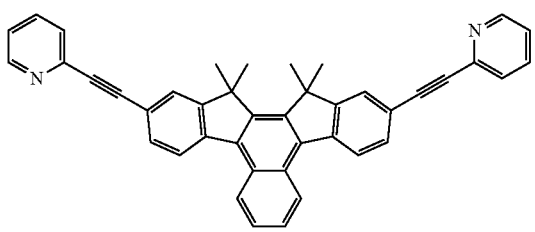

(49)
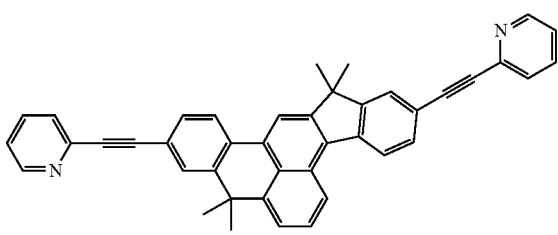

(50)
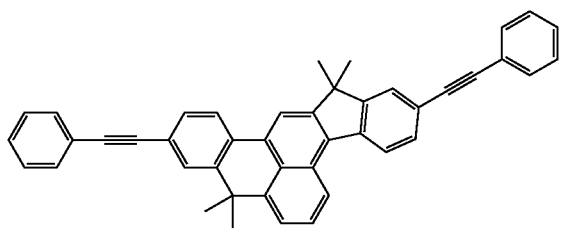

(51)
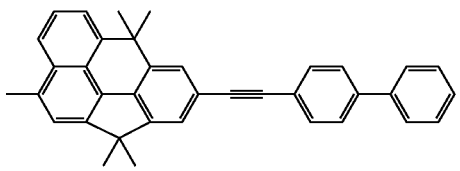

The compounds of the formulae (I) to (XII) according to the invention can be prepared by synthetic steps known to the person skilled in the art. Thus, the various skeletons can be prepared, for example, by a sequence of transition metal-catalysed cross-coupling and subsequent acid-catalysed cyclisation of corresponding tertiary alcohols. The synthetic routes shown in Schemes 1 and 2 below are intended to serve as examples.

The starting compounds used in the synthesis can be, for example, dimethyl 2-bromoisophthalate (Organic Letters 2006, 8(25), 5841-5844) or 4-methylnaphthaleneboronic acid (WO 1999/10339).

Scheme 1:

-continued

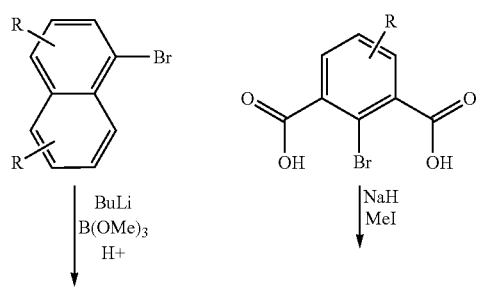

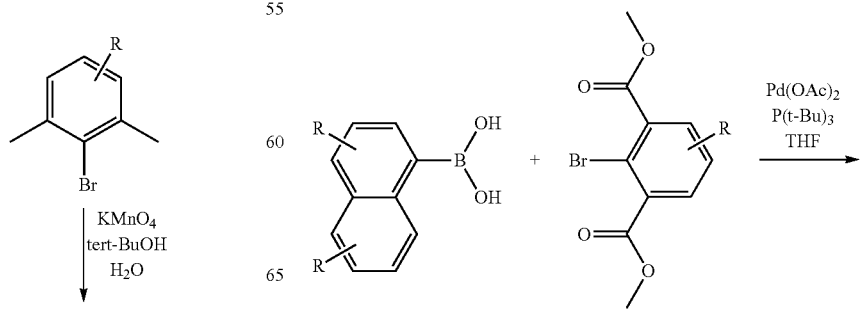

23
-continued
24
-continued
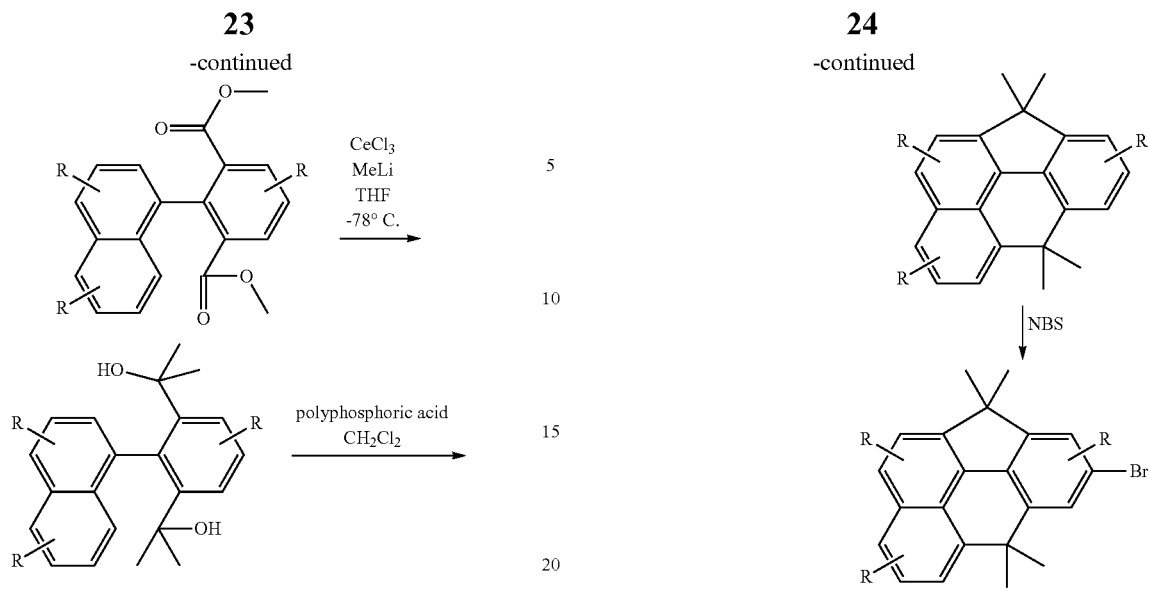
Scheme 2:
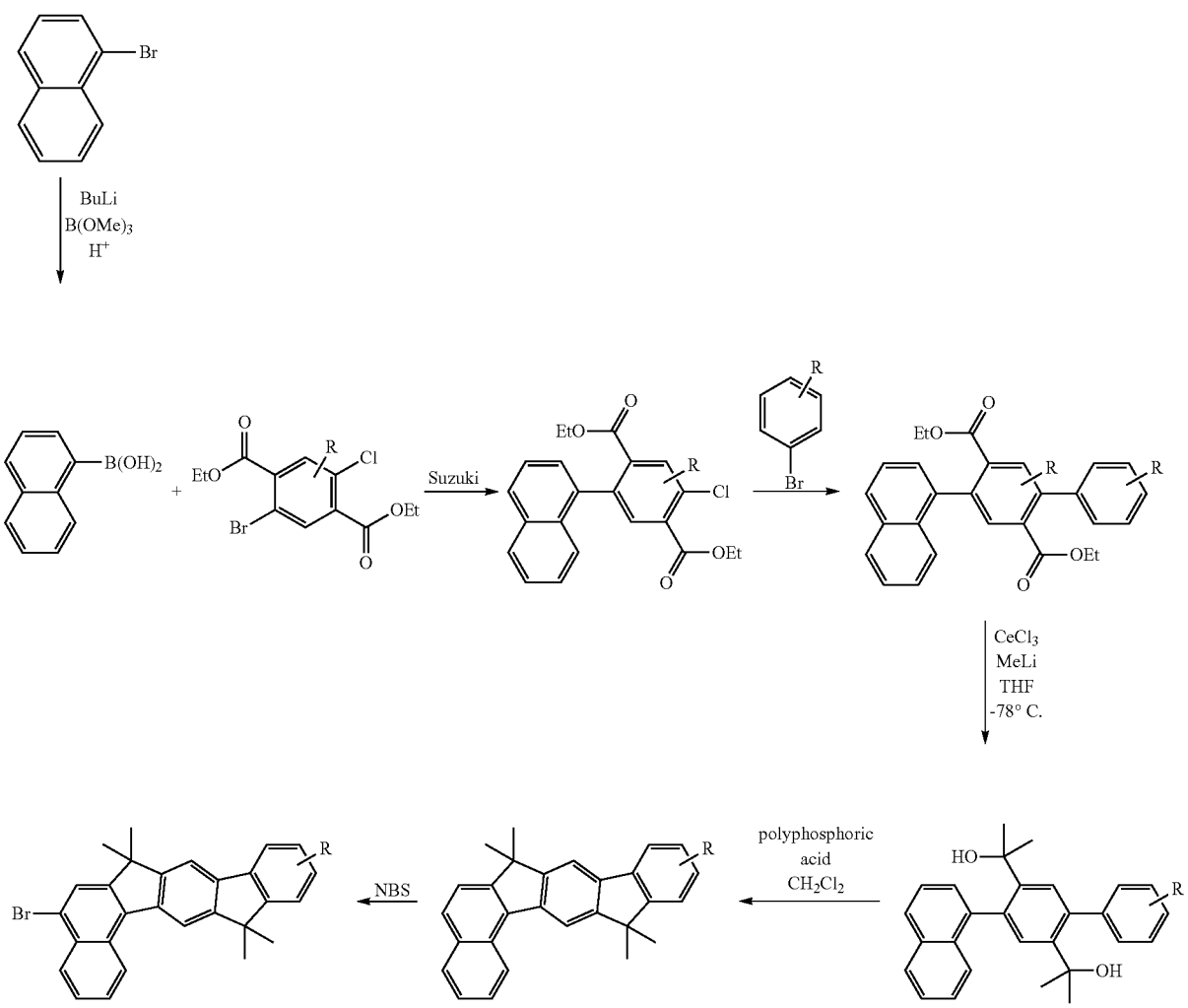

The alkynyl derivatives according to the invention are preferably prepared by Sonogashira coupling of the aryl halides to the corresponding alkyne derivatives in accordance with Scheme 3. The compounds Ar'—Br here correspond to the intermediates shown in Schemes 1 and 2.

Scheme 3:

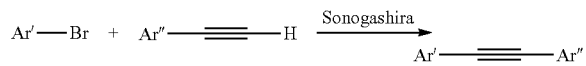

The invention accordingly also relates to a process for the preparation of the compounds of the general formulae (I) to (XII) according to the invention, characterised by the steps of
a) functionalisation of a parent structure obtained, for example, by transition metal-catalysed cross-coupling and subsequent Friedel-Crafts reaction for introduction of the bridges and consisting of a plurality of aromatic rings, by halogenation and
b) a coupling reaction, preferably a Sonogashira reaction, with an alkyne derivative and
c) optionally further steps in order to build up the skeleton or for further functionalisation.

The said steps may also be followed by a polymerisation or oligomerisation reaction.

A process for the preparation of the compounds according to the invention is, in particular, characterised in that a synthetic sequence including at least one coupling reaction between an aryl group and an alkynyl group, preferably including a Sonogashira reaction, is employed.

If polymerisable functional groups are present in the compounds defined above, these can be used for polymerisation of the compounds. In this way, dimers, oligomers, polymers or dendrimers can be prepared. To this end, particular preference is given to compounds which are substituted by reactive leaving groups, such as bromine, iodine, boronic acid or boronic acid ester. These can also be used as comonomers for the preparation of corresponding conjugated, partially conjugated or non-conjugated polymers, oligomers or also as core of dendrimers. The polymerisation here preferably takes place via the halogen functionality or the boronic acid functionality.

For the purposes of this invention, the term oligomer is applied to a compound which has three to nine recurring units. A polymer in the sense of the invention is taken to mean a compound which has ten or more recurring units.

The invention correspondingly furthermore relates to dimers, oligomers, polymers or dendrimers comprising one or more compounds of the formulae (I) to (XII), as defined above, where a bond to a radical R in the compounds of the formulae (I) to (XII) is replaced by the bond to the adjacent recurring unit. Depending on the linking of the compounds, the compounds are part of a main chain of an oligomer or polymer or a side chain of an oligomer or polymer or dendrimer or represent an end group of an polymer, oligomer or dendrimer. The oligomers, polymers or dendrimers may be conjugated, partially conjugated or non-conjugated. The oligomers or polymers may be linear, branched or dendritic. In the linearly linked structures, the units of the formulae (I) to (XII) may either be linked directly to one another or they may be linked to one another via a divalent group, for example via a substituted or unsubstituted alkylene group, via a heteroatom or via a divalent aromatic or heteroaromatic group. In branched structures, for example, three or more units of the formulae (I) to (XII) may be linked via a trivalent or polyvalent group, for example via a trivalent or polyvalent aromatic or heteroaromatic group, to form a branched oligomer or polymer.

The same preferred embodiments as described above apply to the recurring units of the formulae (I) to (XII) in oligomers and polymers.

For the preparation of the oligomers, polymers or dendrimers, the functionalised compounds of the general formulae (I) to (XII) are homopolymerised or copolymerised with further monomers. In the case of the preparation of copolymers, it is preferred for the compounds of the formulae (I) to (XII) to be present in the range from 0.1 to 50 mol %. Suitable and preferred comonomers are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or DE 102005037734) or also a plurality of these units. These polymers usually also comprise further units, for example emitting (fluorescent or phosphorescent) units, such as, for example, vinyltriarylamines (for example in accordance with DE 102005060473) or phosphorescent metal complexes (for example in accordance with WO 06/003000), and/or charge-transport units, in particular those based on triarylamines.

Since either one or two halogen functionalities, preferably bromine, can be introduced selectively into the compounds according to the invention, it is possible to build up dimers, trimers, tetramers, pentamers, etc. specifically. Thus, for example, two monofunctionalised compounds can be coupled in a Suzuki coupling or a Yamamoto coupling to give the corresponding dimers. The corresponding tetramers are accessible selectively by halogenation and further coupling to monofunctionalised compounds. Furthermore, two monofunctionalised compounds can be coupled to a difunctionalised compound to give the corresponding trimer. The coupling reaction here is preferably a Suzuki coupling. The corresponding pentamers are accessible selectively by halogenation, preferably bromination, and further coupling to monofunctionalised compounds. It is likewise possible to functionalise the dimers, trimers, tetramers, pentamers, etc. further by, for example, halogenating them and reacting them with a diarylamine in a Hartwig-Buchwald coupling to give the corresponding aromatic amines.

The invention furthermore relates to formulations comprising at least one compound of one of the formulae (I) to (XII) and/or at least one oligomer, polymer or dendrimer comprising at least one compound of one of the formulae (I) to (XII) and at least one solvent, preferably an organic solvent.

The invention furthermore relates to the use of the compounds according to the invention or the use of dimers, oligomers, polymers or dendrimers comprising the compounds according to the invention in an electronic device. The electronic device is preferably an organic electroluminescent device (OLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC)

or an organic laser diode (O-laser). Use in an organic electroluminescent device (OLED) is particularly preferred.

The compounds according to the invention are preferably used within the electronic device as dopant, as matrix material, as hole-transport compound and/or as electron-transport compound.

On use as hole-injection or hole-transport material, the compounds according to the invention preferably contain one or more electron-donating groups, for example diarylamino groups. On use as electron-transport materials, the compounds according to the invention preferably contain one or more electron-withdrawing groups, for example imidazole, benzimidazole or triazine derivatives. For use as matrix material for fluorescent or phosphorescent dopants, the compounds according to the invention are preferably suitable in their unsubstituted form or monoaromatically or aliphatically substituted form. For use as dopant, it is preferred for at least one substituent R to be a diarylamino group $N(Ar)_2$ or a $CR^1=CR^1Ar$ group.

The invention furthermore relates to the use of the compounds according to the invention as charge-transport material and/or charge-injection material, preferably in a corresponding layer. A layer of the electronic device which comprises one or more of the compounds according to the invention can be either a hole-transport layer, a hole-injection layer, an electron-transport layer or an electron-injection layer. The use as charge-blocking material, for example hole-blocking material or electron-blocking material, and as exciton-blocking material, is also possible.

The invention furthermore relates to electronic devices or organic electroluminescent devices (organic light-emitting diodes or polymeric light-emitting diodes, OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), but in particular organic electroluminescent devices (=organic light-emitting diodes, OLEDs), comprising one or more compounds of the formulae (I) to (XII), as defined above.

The organic electroluminescent device according to the invention comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p-n junctions. One or more interlayers which have, for example, an exciton-blocking function may likewise be introduced between two emitting layers. However, it should be pointed out that each of these layers does not necessarily have to be present. These layers may comprise compounds of the general formulae (I) to (XII), as defined above.

In a preferred embodiment of the invention, the compounds of the formulae (I) to (XII) are employed as emitting compounds in an emitting layer. The organic electroluminescent device here may comprise one emitting layer or a plurality of emitting layers, where at least one emitting layer preferably comprises at least one compound of the formulae (I) to (XII), as defined above. However, the compounds according to the invention may also be present exclusively in layers other than the emitting layer, for example in an electron-transport layer or a hole-transport layer.

If a plurality of emission layers are present, these preferably have in total a plurality of emission maxima between 380 nm and 750 nm, resulting overall in white emission. Various emitting compounds which are able to fluoresce or phosphoresce can be used in the emitting layers. Particular preference is given to three-layer systems, where the three layers exhibit blue, green and orange or red emission (for the basic structure, see, for example, WO 05/011013).

If the compounds of the formulae (I) to (XII) are employed as emitting compounds in an emitting layer, the compounds are preferably used in combination with one or more matrix materials (=host materials). A matrix material in a system comprising matrix (host) and dopant (=emitter) is taken to mean the component which is present in the system in the higher proportion. In a system comprising a matrix material and a plurality of dopants, the matrix material is taken to mean the component whose proportion in the mixture is the highest.

In these cases, the mixture comprising compounds of the formulae (I) to (XII) and the matrix material comprises between 1 and 50% by vol., preferably between 2 and 50% by vol., particularly preferably between 3 and 40% by vol., in particular between 5 and 15% by vol., of the compounds of the formulae ((I) to (XII), based on the entire mixture comprising dopant and matrix material. Correspondingly, the mixture comprises between 99 and 50% by vol., preferably between 98 and 50% by vol., particularly preferably between 97 and 60% by vol., in particular between 95 and 85% by vol., of the matrix material, based on the entire mixture comprising dopant and matrix material.

Suitable matrix materials (host materials) are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) the benzanthracenes (for example in accordance with DE 102007024850) or the benzophenanthrenes (for example in accordance with the unpublished application DE 102009005746.3). Particularly preferred matrix materials are selected from the classes of the oligoarylenes comprising naphthalene, anthracene, benzanthracene, benzophenanthrene and/or pyrene or atropisomers of these compounds, the ketones, the phosphine oxides and the sulfoxides. Very particularly preferred matrix materials are selected from the classes of the oligoarylenes comprising anthracene, benzanthracene, benzophenanthrene and/or pyrene or atropisomers of these compounds. For the purposes of this invention, an oligoarylene is intended to be taken to mean a compound in which at least three aryl or arylene groups are bonded to one another. Very particular preference is given to 9,10-diarylanthracene derivatives in which at least one aryl group is a condensed aryl group, or 2,9,10-triarylanthracene derivatives in which at least one aryl group is a condensed aryl group.

Suitable matrix materials, preferably for fluorescent dopants, are, for example, the materials depicted in the following table, and derivatives of these materials, as disclosed in WO 04/018587, WO 08/006449, U.S. Pat. No. 5,935,721, US 2005/0181232, JP 2000/273056, EP 681019, US 2004/0247937 and US 2005/0211958.
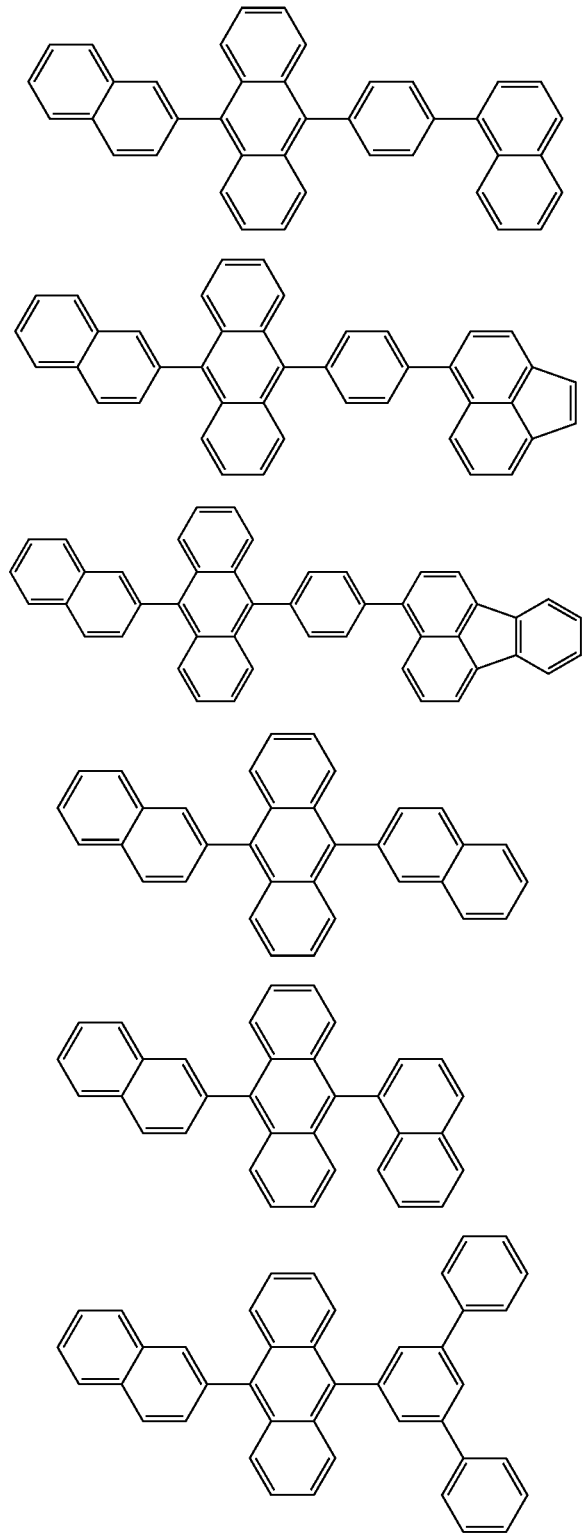
-continued
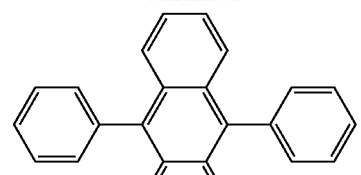
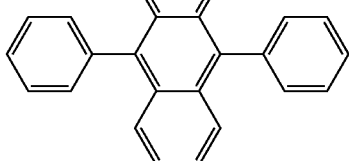
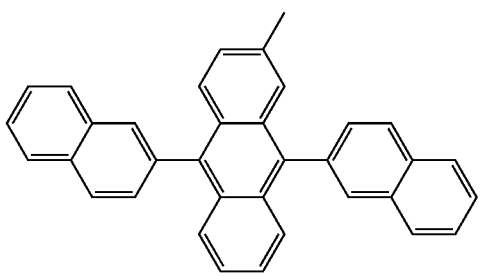
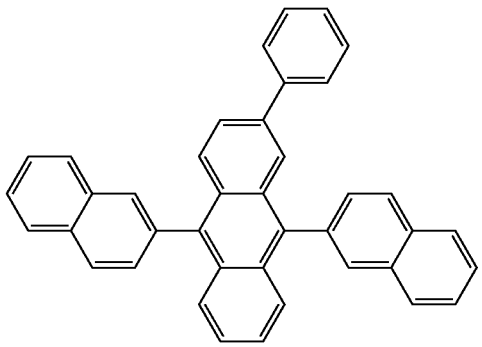
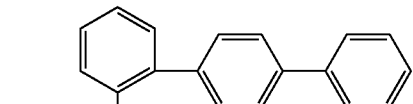
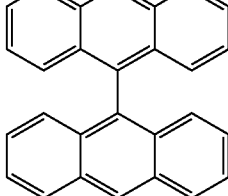
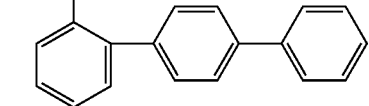

-continued
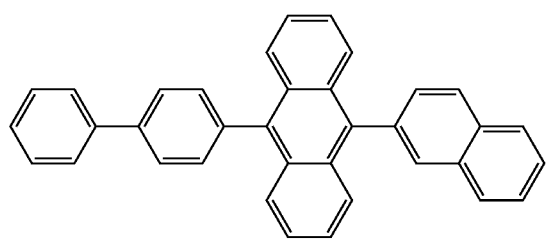
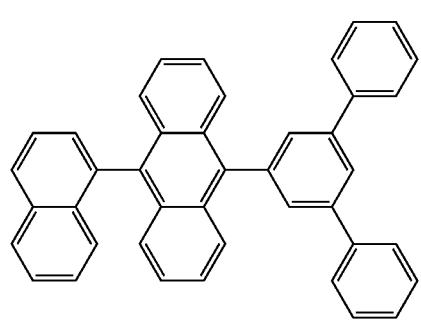
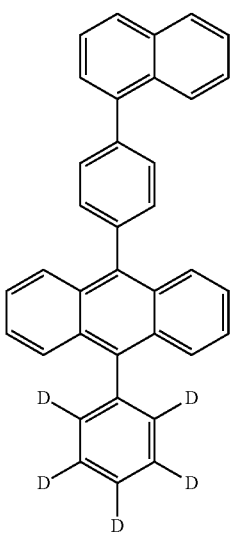
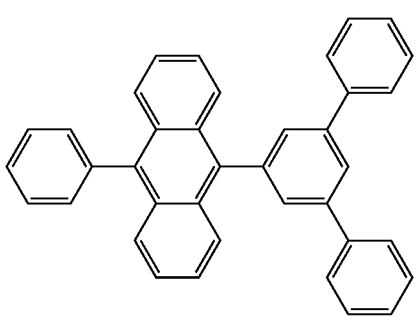
-continued
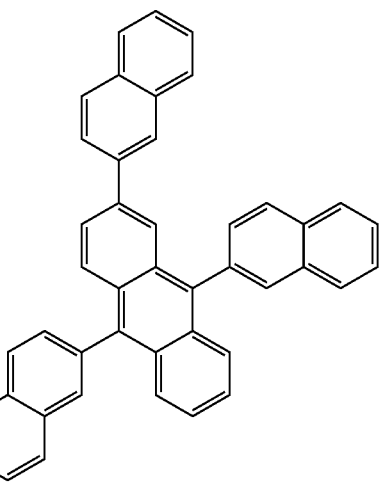
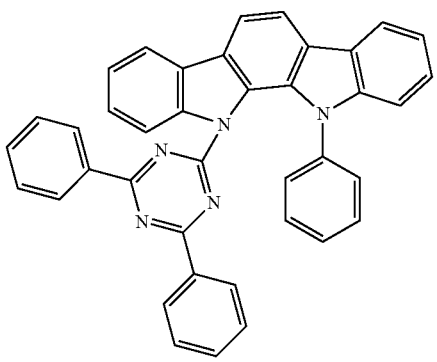
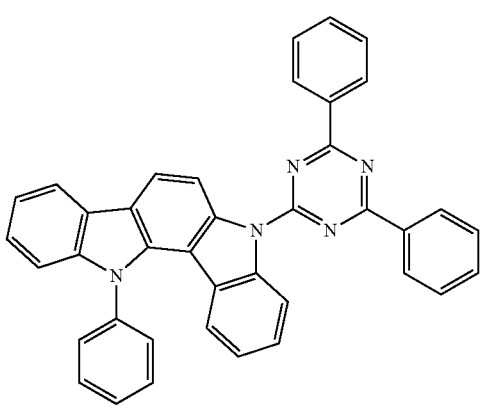
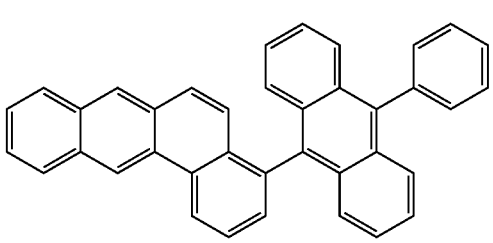

-continued
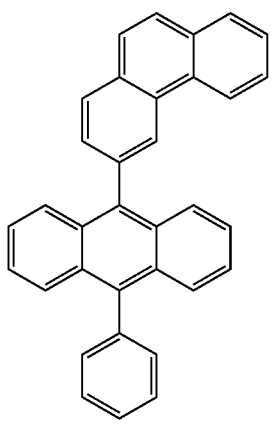
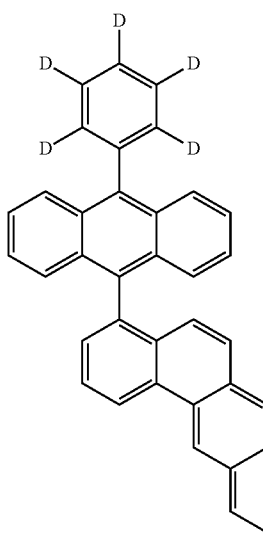
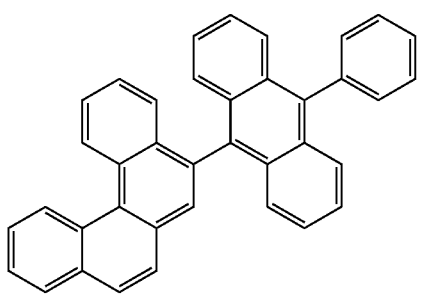
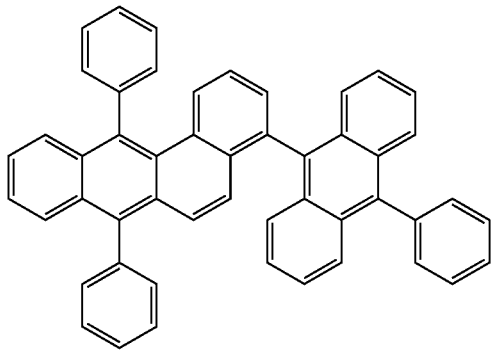
-continued
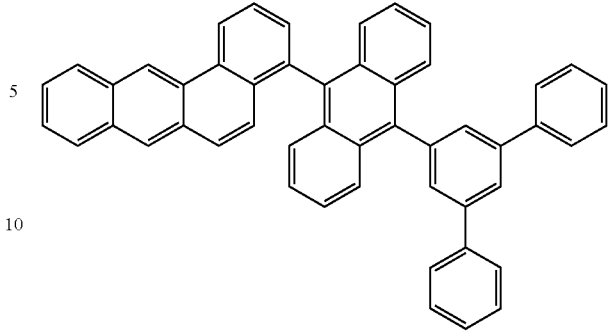
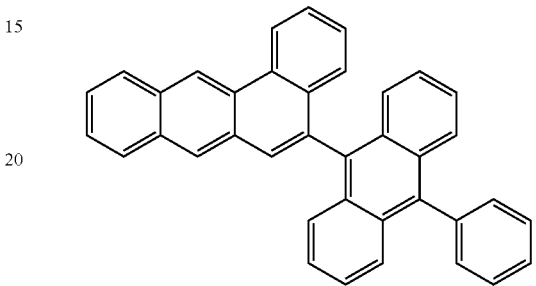
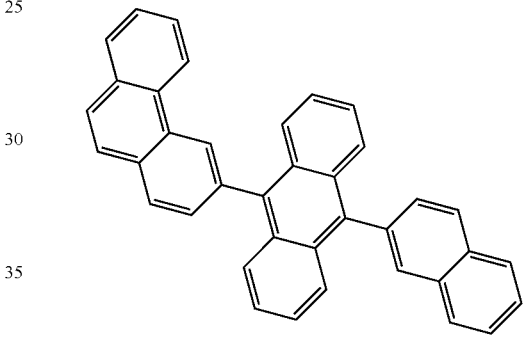
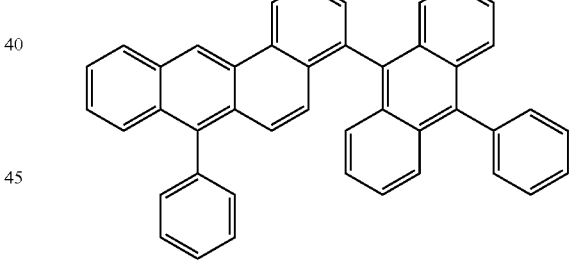
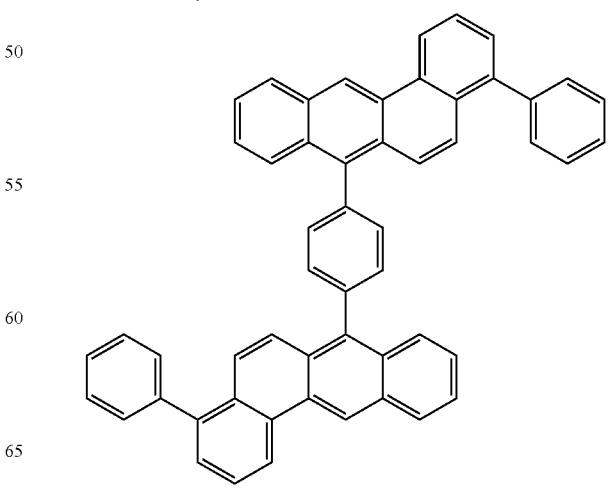

35
-continued
36
-continued
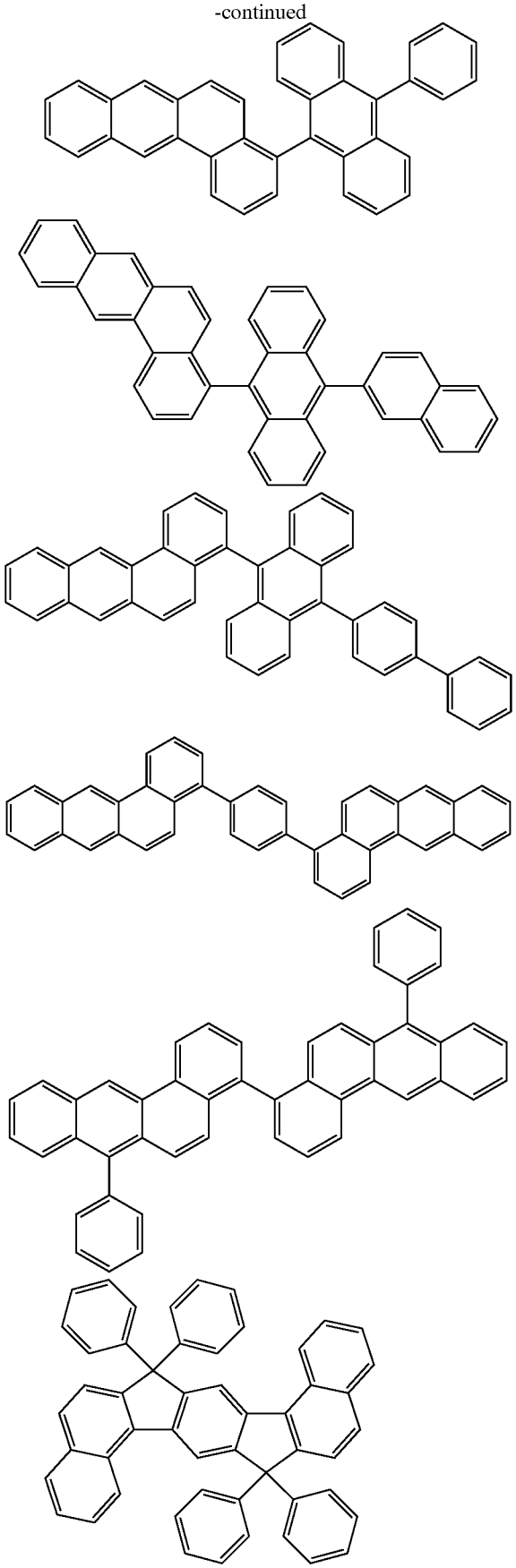
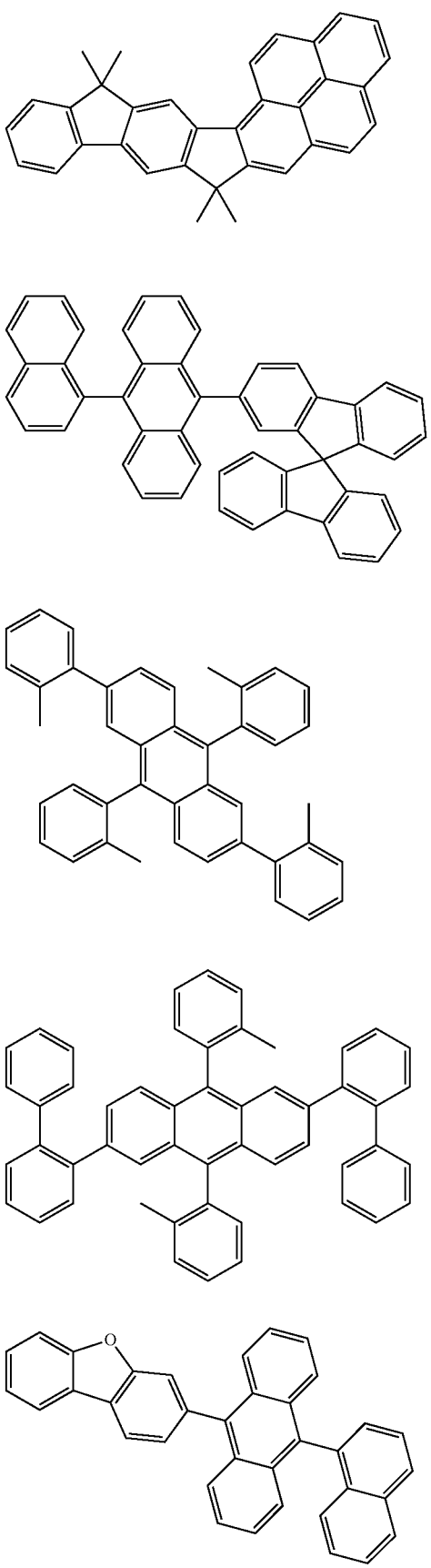

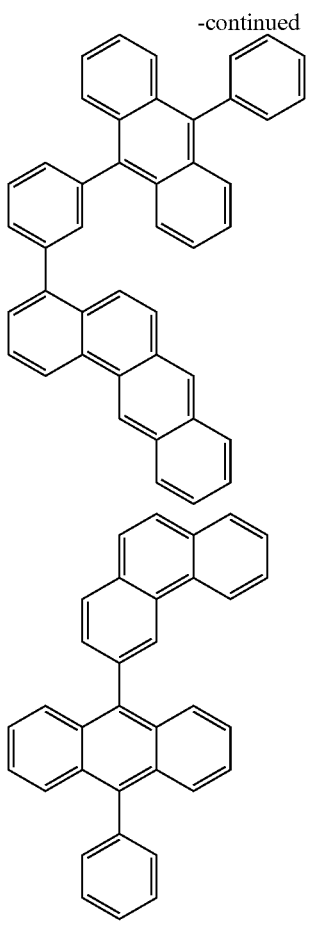

A further preferred application is the use of the compound as matrix material for fluorescent or phosphorescent dopants, in particular for fluorescent dopants.

The proportion of the matrix material of the formulae (I) to (XII) in the emitting layer is then between 50.0 and 99.9% by vol., preferably between 80.0 and 99.5% by vol., particularly preferably between 90.0 and 99.0% by vol. Correspondingly, the proportion of the dopant is between 0.1 and 50.0% by vol., preferably between 0.5 and 20.0% by vol., particularly preferably between 1.0 and 10.0% by vol.

Preferred fluorescent dopants are, besides the compounds according to the invention, selected from the class of the monostyrylamines, the distyrylamines, the tristyrylamines, the tetrastyrylamines and the arylamines. A monostyrylamine is taken to mean a compound which contains one styryl group and at least one amine, which is preferably aromatic. A distyrylamine is taken to mean a compound which contains two styryl groups and at least one amine, which is preferably aromatic. A tristyrylamine is taken to mean a compound which contains three styryl groups and at least one amine, which is preferably aromatic. A tetrastyrylamine is taken to mean a compound which contains four styryl groups and at least one amine, which is preferably aromatic. For the purposes of this invention, an arylamine or an aromatic amine is taken to mean a compound which contains three aromatic or heteroaromatic ring systems bonded directly to the nitrogen, at least one of which is preferably a condensed ring system having at least 14 aromatic ring atoms. The styryl groups are particularly preferably stilbenes, which may also be substituted further on the double bond or on the aromatic system. Examples of dopants of this type are substituted or unsubstituted tristilbenamines or further dopants which are described, for example, in WO 06/000388, WO 06/058737, WO 06/000389, WO 07/065549 and WO 07/115610. Preferred dopants are furthermore compounds in accordance with WO 06/122630. Preferred dopants are furthermore diarylamine derivatives or bis(diarylamine) derivatives of monobenzoindenofluorene or dibenzoindenofluorene, for example in accordance with WO 08/006449 or WO 07/140847. Dopants which are again furthermore preferred are the compounds disclosed in DE 102008035413.

In a further embodiment of the invention, the compounds of the formulae (I) to (XII) are employed as matrix materials for phosphorescent dopants. In this case, one or more substituents R and/or bridges X preferably contain at least one group $C=O$, $P(=O)$, $SO_2$ and/or $Ar^1$, of these preferably triazine. These groups are particularly preferably bonded directly to the central unit according to the invention and furthermore particularly preferably contain one or, in the case of phosphine oxide, two further aromatic substituents.

In phosphorescent devices, the dopant is preferably selected from the class of the metal complexes containing at least one element having an atomic number of greater than 20, preferably greater than 38 and less than 84, particularly preferably greater than 56 and less than 80. Preference is given to the use of metal complexes which contain copper, molybdenum, tungsten, rhenium, ruthenium, osmium, rhodium, iridium, palladium, platinum, silver, gold or europium, in particular iridium, platinum or copper. Phosphorescent materials as used in accordance with the prior art are generally suitable for this purpose.

The phosphorescent dopant is particularly preferably selected from compounds of the formulae (P1) to (P4)

formula (P1)

formula (P2)

formula (P3)

formula (P4)

where:

DCy is, identically or differently on each occurrence, a cyclic group which contains at least one donor atom, preferably nitrogen, carbon in the form of a carbene or phosphorus, via which the cyclic group is bonded to the metal, and which may in turn carry one or more substituents R; the groups DCy and CCy are connected to one another via a covalent bond;

CCy is, identically or differently on each occurrence, a cyclic group which contains a carbon atom via which the cyclic group is bonded to the metal and which may in turn carry one or more substituents R;

A is, identically or differently on each occurrence, a monoanionic, bidentate-chelating ligand, preferably a diketonate ligand;

R is as defined above.

Further examples of phosphorescent dopants are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art can also employ, without inventive step, further phosphorescent complexes in combination with the compounds according to the invention in organic electroluminescent devices.

A possible further use of compounds of the formulae (I) to (XII) is the use as hole-transport or hole-injection material in a hole-transport or hole-injection layer. This use is particularly preferred if one or more bridges X stand for S or NR and/or if one or more radicals R stand for N(Ar)$_2$. Compounds of this type can furthermore also be employed in an electron-blocking layer.

A further possible use of compounds of the formulae (I) to (XII) is the use as electron-transport material in an electron-transport layer. Suitable for this purpose are, in particular, compounds of the formulae (I) to (XII) which are substituted by at least one electron-deficient heteroaromatic group. Electron-deficient heteroaromatic groups are preferably 6-membered heteroaromatic rings having at least one nitrogen atom and corresponding condensed systems, for example pyridine, pyrazine, pyrimidine, pyridazine, triazine, quinoline, quinoxaline or phenanthroline, or 5-membered heteroaromatic rings having at least one nitrogen atom and one further heteroatom selected from N, O and S, and corresponding condensed systems, for example pyrazole, imidazole, oxazole, oxadiazole or benzimidazole. If the compounds of the formulae (I) to (XII) are used as electron-transport material, the bridge X preferably stands for C(R)$_2$. The compounds are furthermore preferably suitable as electron-transport materials if at least one bridge X, preferably both bridges X, stand(s) for C=O, P(=O)R, SO or SO$_2$. Compounds according to the invention of this type can preferably also be employed in a hole-blocking layer.

The materials which are preferably employed in the electronic devices according to the invention for the respective functions or in the respective functional layers are indicated below. Furthermore, the preferred uses indicated above for the compounds according to the invention apply here.

Besides the compounds according to the invention, suitable charge-transport materials, as can be used in the hole-injection or hole-transport layer or in the electron-transport layer of the organic electroluminescent device according to the invention, are, for example, the compounds disclosed in Y. Shirota et al., *Chem. Rev.* 2007, 107(4), 953-1010, or other materials as employed in these layers in accordance with the prior art.

Examples of preferred hole-transport materials which can be used in a hole-transport or hole-injection layer in the electroluminescent device according to the invention are indenofluorenamines and derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic ring systems (for example in accordance with U.S. Pat. No. 5,061, 569), the amine derivatives disclosed in WO 95/09147, monobenzoindenofluorenamines (for example in accordance with WO 08/006449) or dibenzoindenofluorenamines (for example in accordance with WO 07/140847). Hole-transport and hole-injection materials which are furthermore suitable are derivatives of the compounds depicted above, as disclosed in JP 2001/226331, EP 676461, EP 650955, WO 01/049806, U.S. Pat. No. 4,780,536, WO 98/30071, EP 891121, EP 1661888, JP 2006/253445, EP 650955, WO 06/073054 and U.S. Pat. No. 5,061,569.

Suitable hole-transport or hole-injection materials are furthermore, for example, the materials listed in the following table.

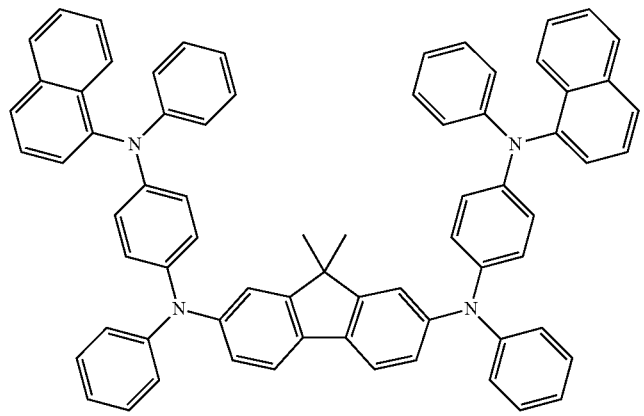

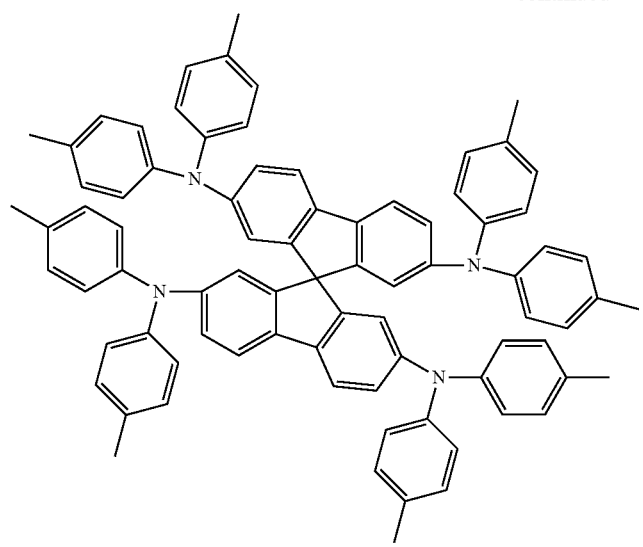
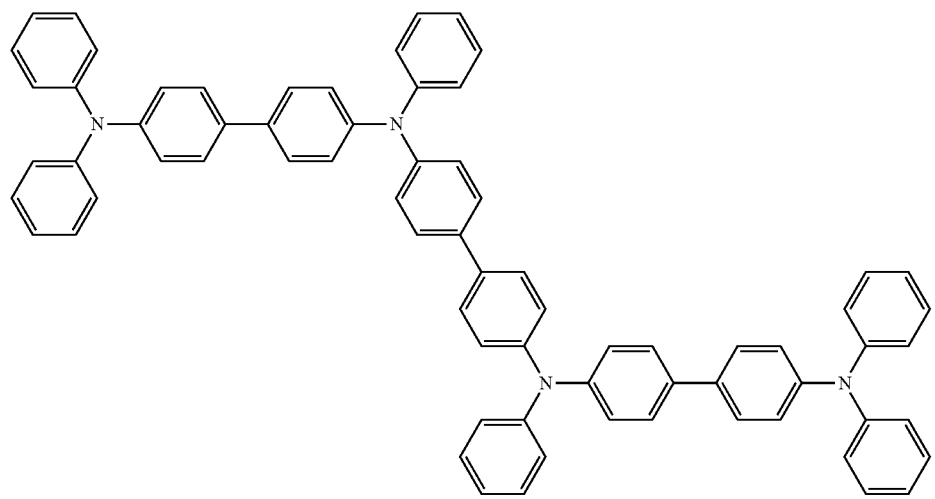
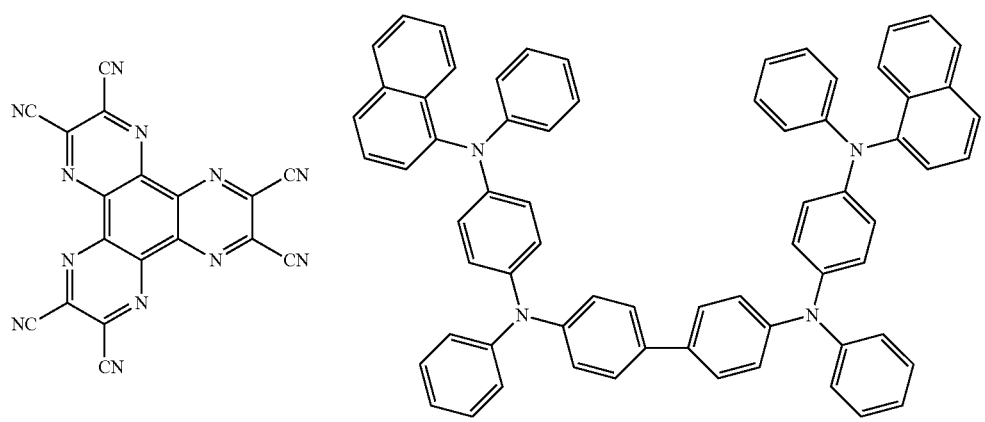

-continued
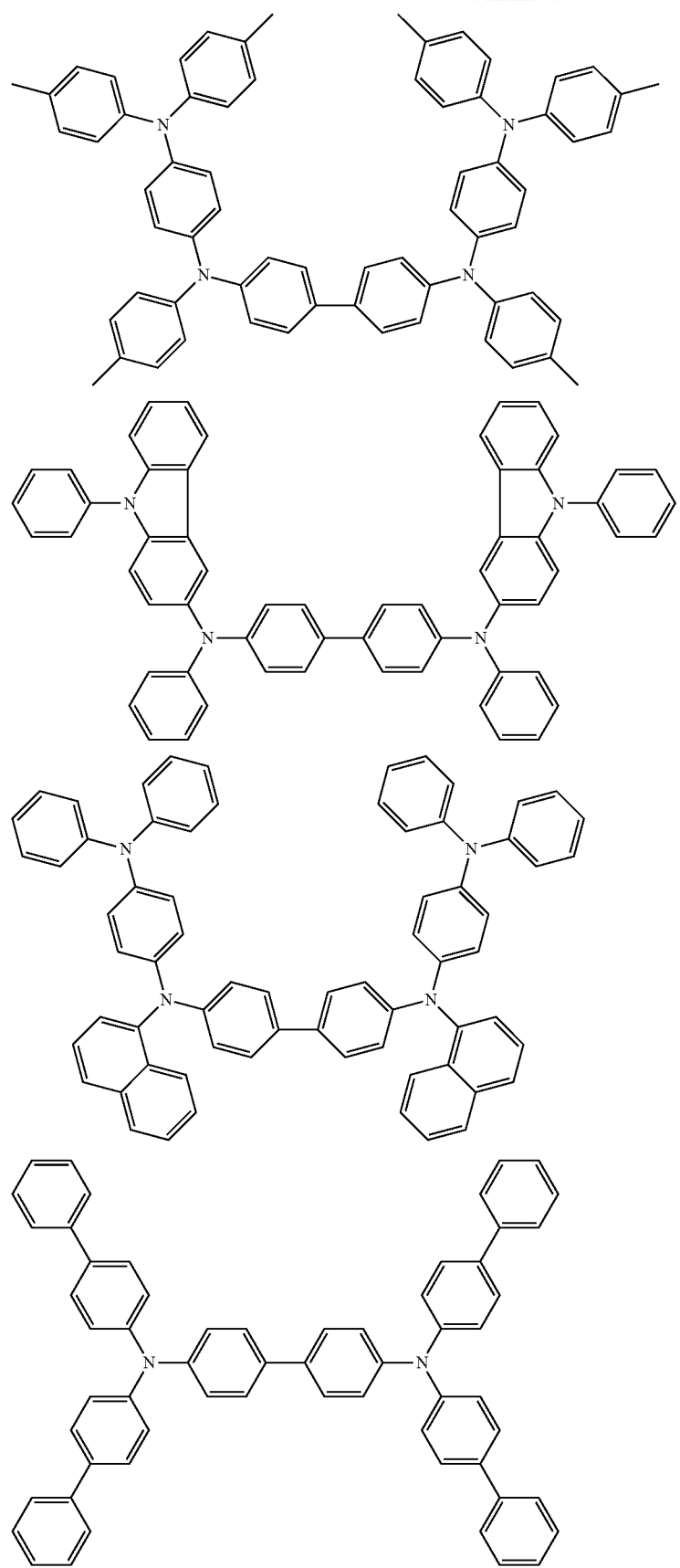

-continued
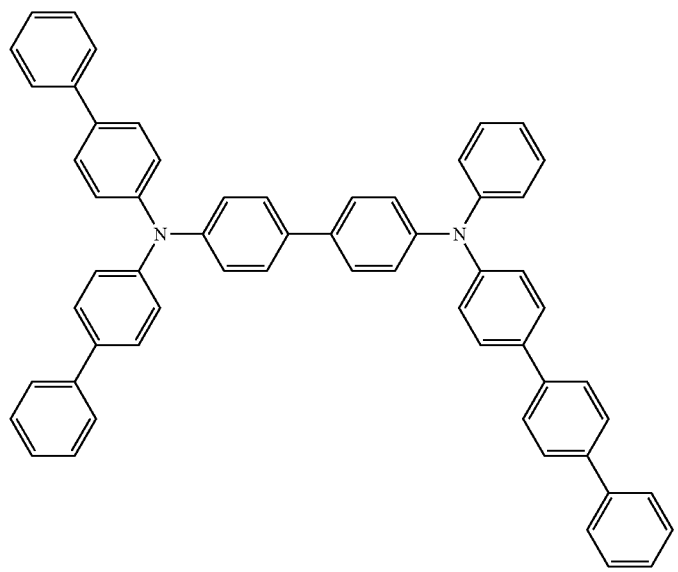
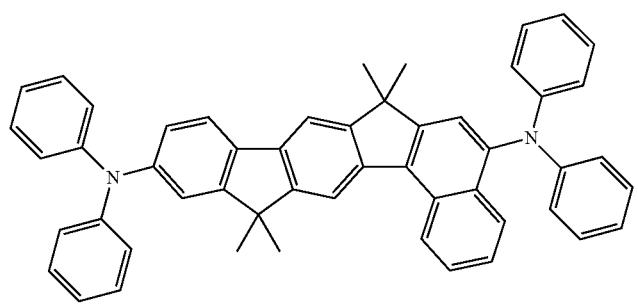
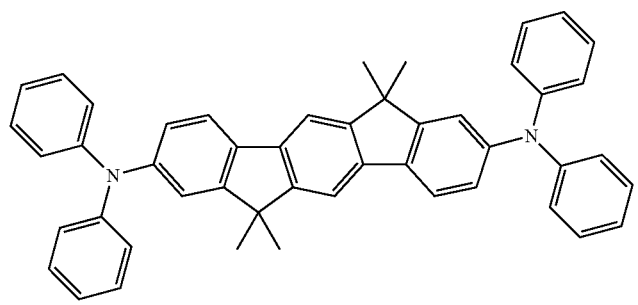
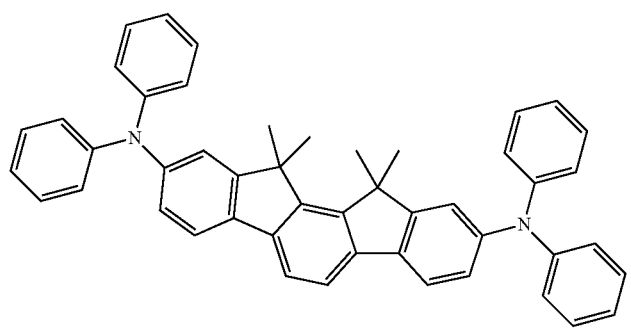

-continued
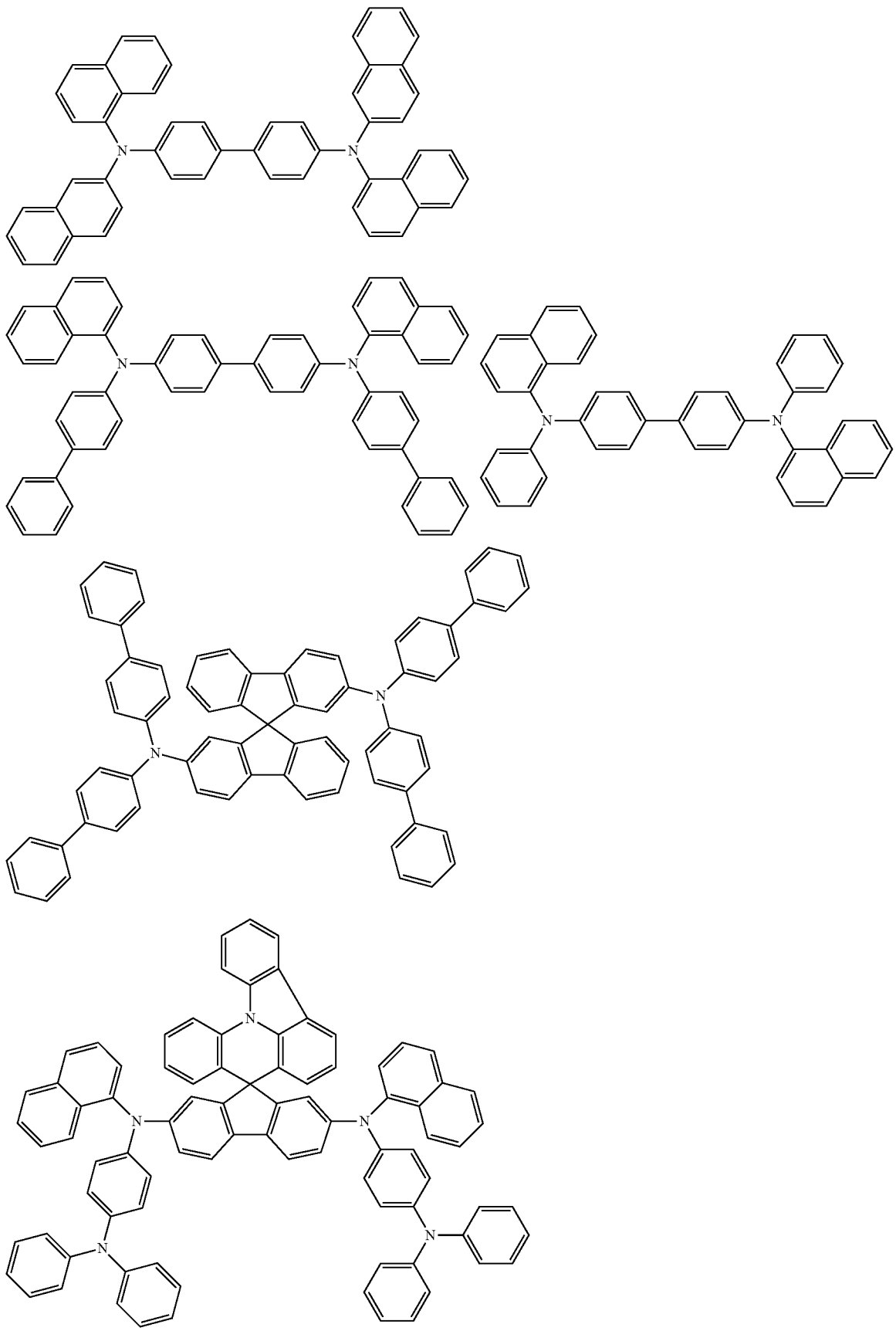

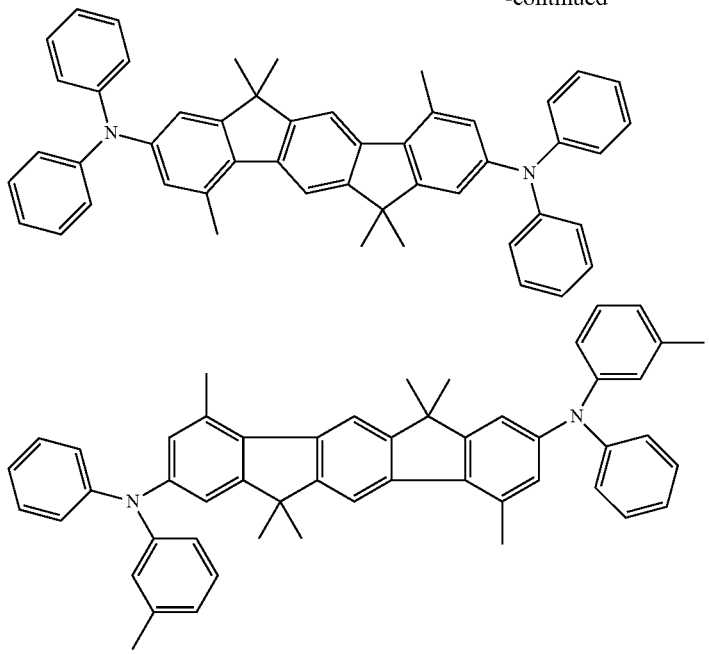
Suitable electron-transport or electron-injection materials which can be used in the electroluminescent device according to the invention are, for example, the materials indicated in the following table. Electron-transport and electron-injection materials which are furthermore suitable are, for example, AlQ$_3$, BAlQ, LiQ and LiF.
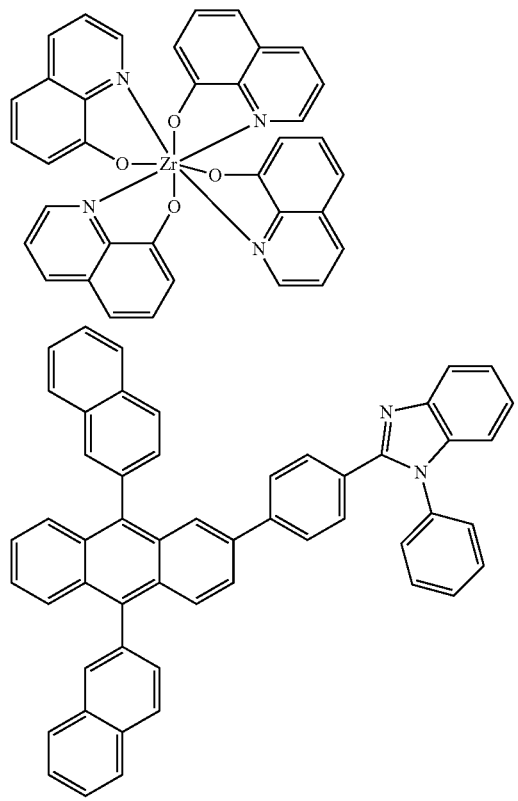
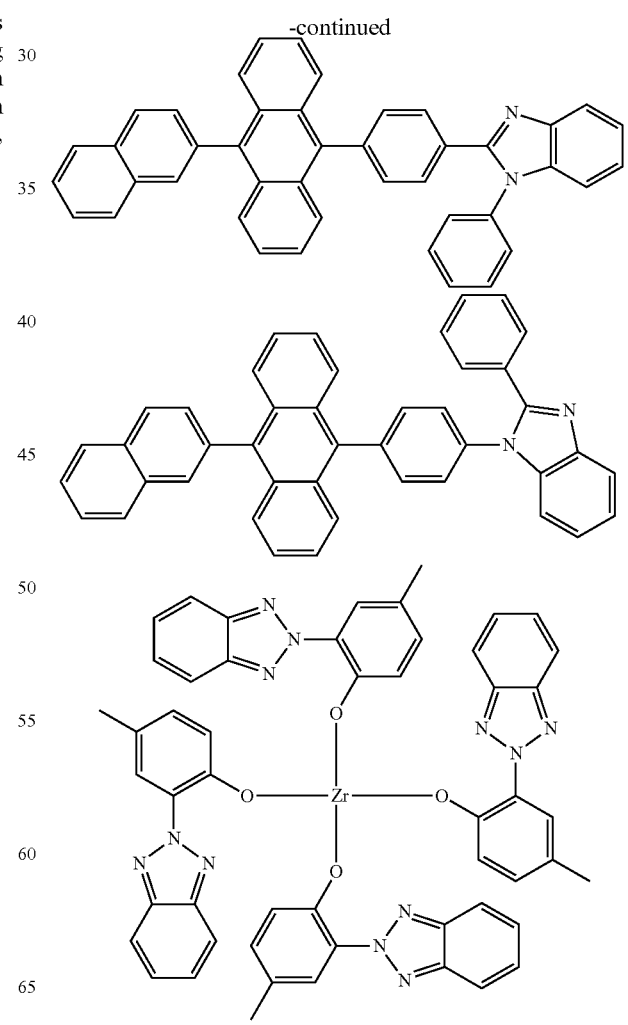

51
-continued
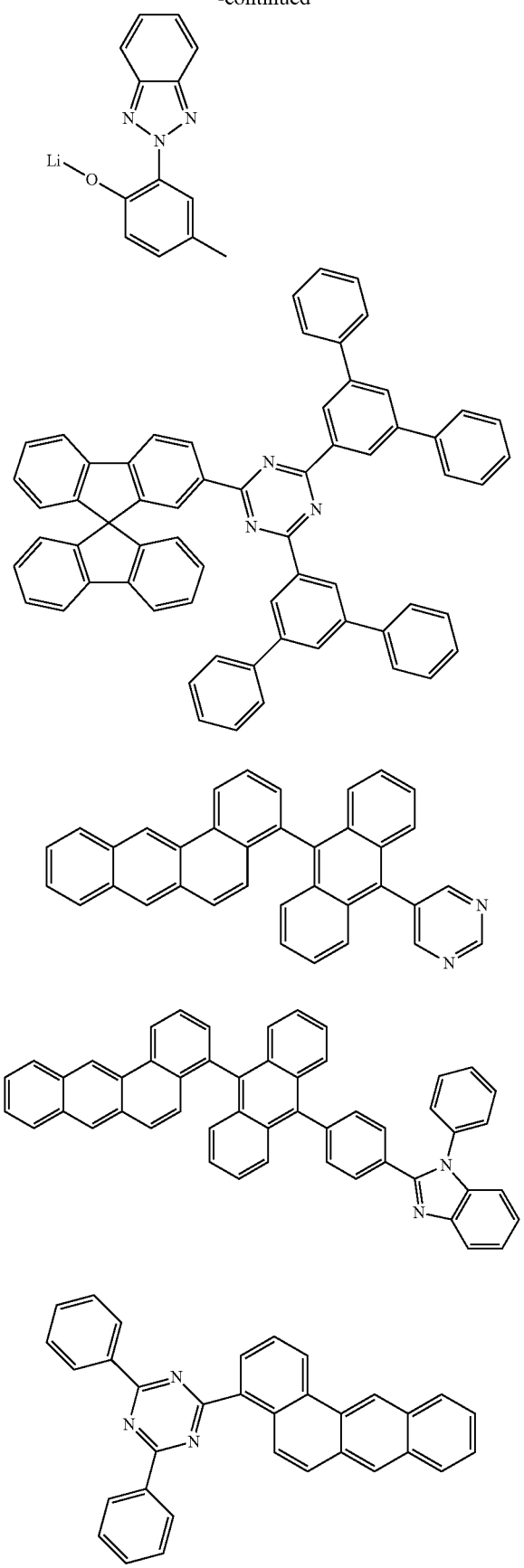
52
-continued
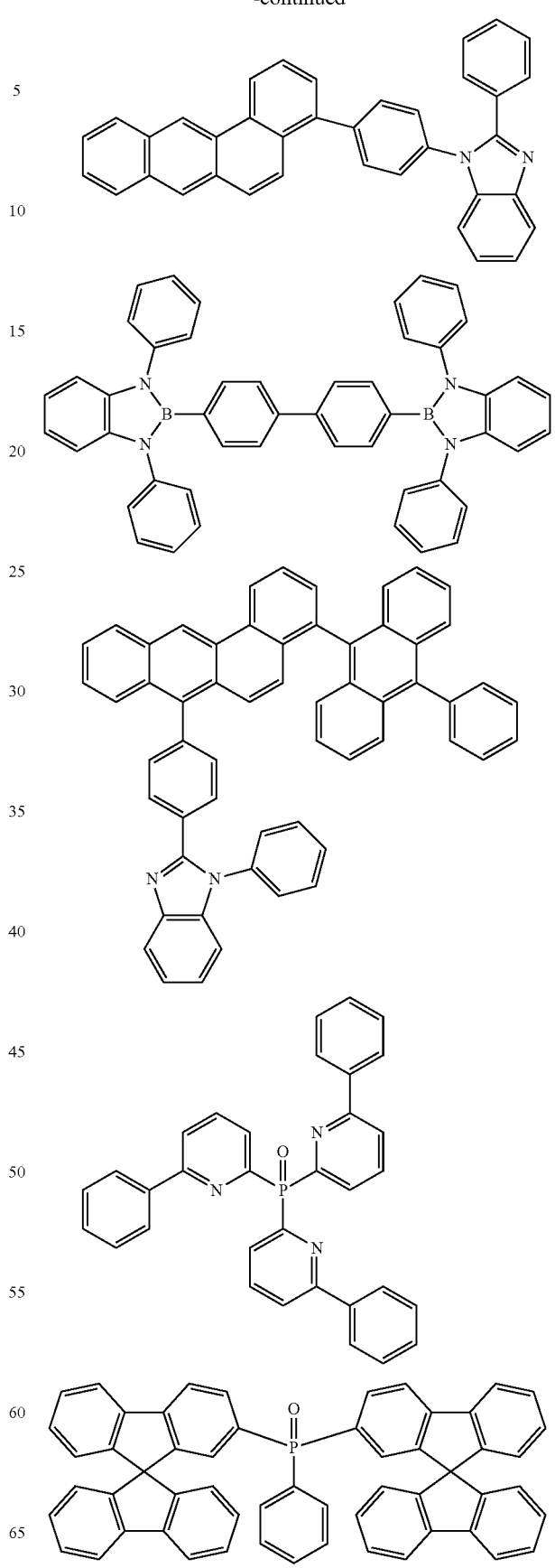

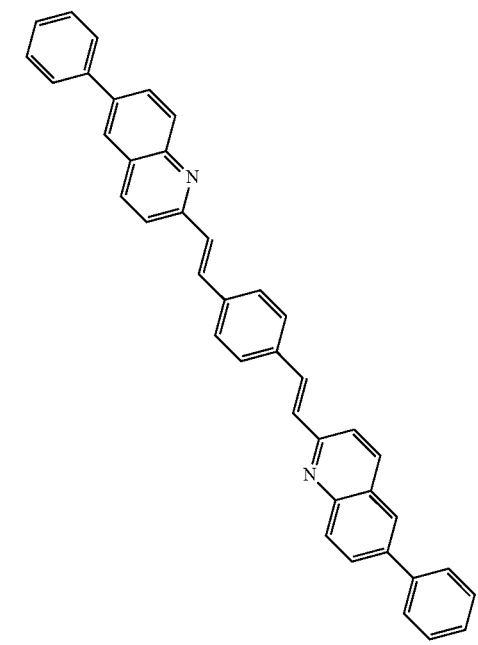
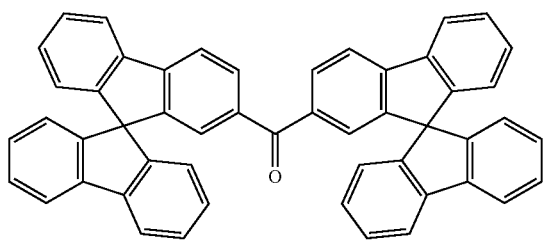
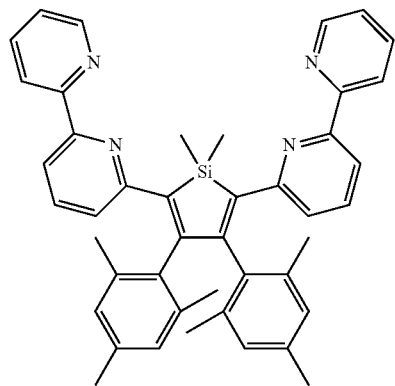
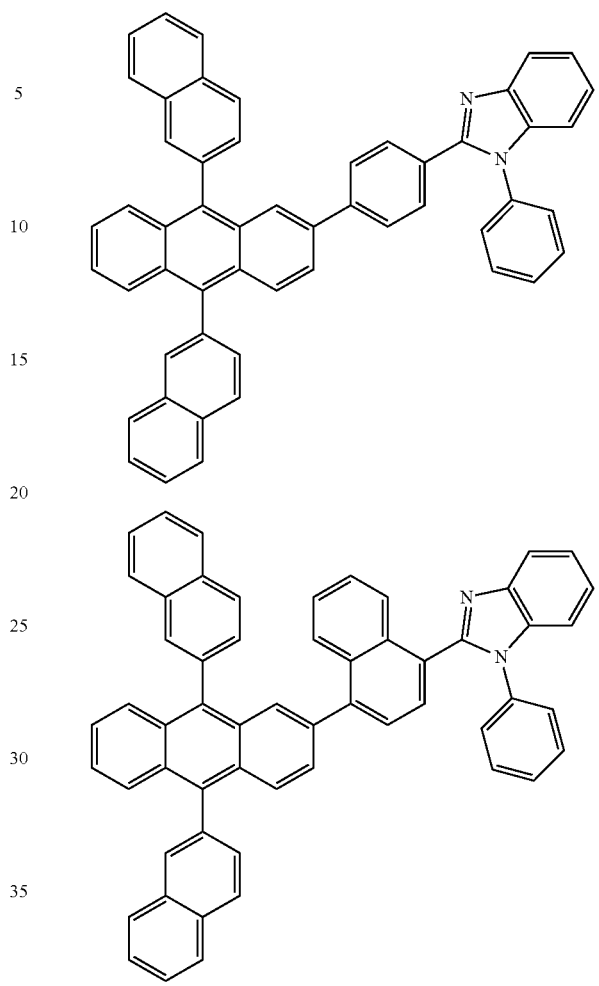
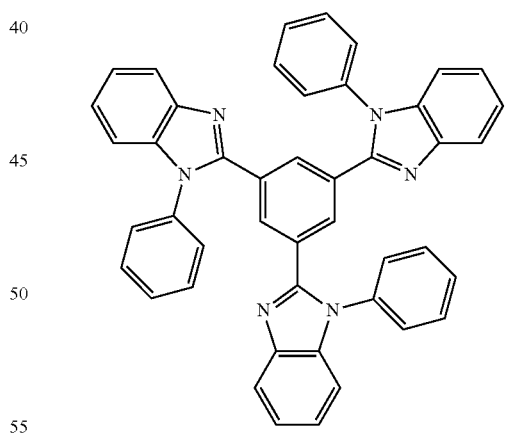
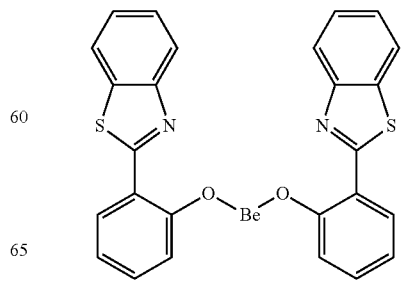

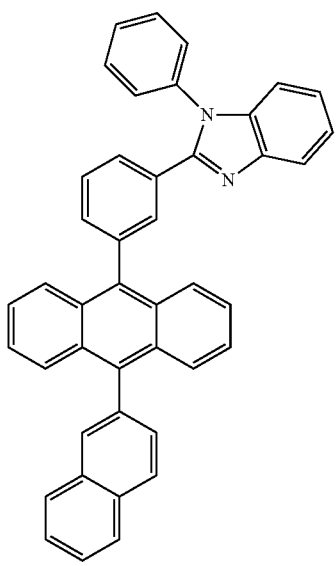

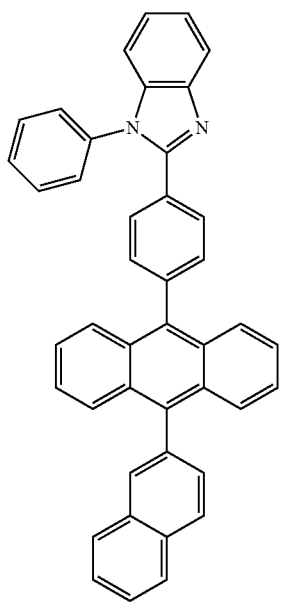

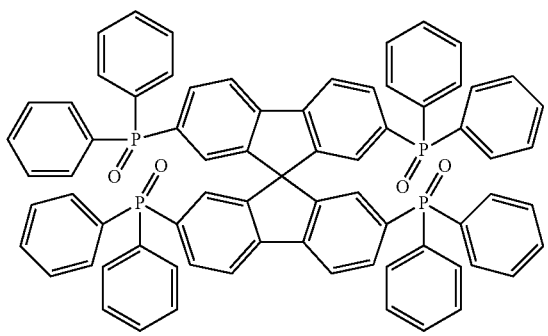

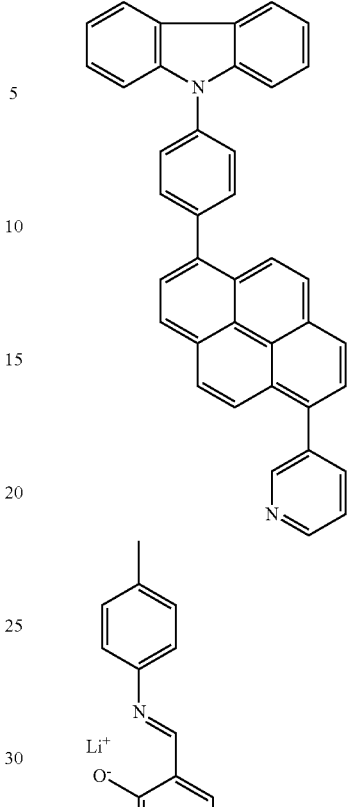

The cathode of the electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Alloys comprising an alkali metal or alkaline-earth metal and sliver, for example an alloy comprising magnesium and silver, are furthermore suitable. In the case of multilayered structures, further metals which have a relatively high work function, such as, for example, Ag or Al, may also be used in addition to the said metals, in which case combinations of the metals, such as, for example, Ca/Ag, Mg/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Lithium quinolinate (LiQ) can furthermore be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cell) or the coupling-out of light (OLED, O-LASER).

Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

Preference is furthermore given to an organic electroluminescent device in which one or more layers are applied by a sublimation process, in which the materials are vapour-deposited in vacuum sublimation units at an initial pressure of less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterised in that one or more layers are applied by the OVPD (organic vapour phase deposition) process or with the aid of carrier-gas sublimation, in which the materials are applied at a pressure between $10^{-5}$ mbar and 1 bar.

Preference is furthermore given to an organic electroluminescent device, characterised in that one or more layers are produced from solution, such as, for example, by spin coating, or by any desired printing process, such as, for example, screen printing, flexographic printing or offset printing, but particularly preferably LITI (light induced thermal imaging, thermal transfer printing) or ink-jet printing. Soluble compounds, which are obtained by suitable substitution, are necessary for this purpose. These methods are also suitable, in particular, for the use of oligomers and polymers comprising the compounds according to the invention in organic electroluminescent devices.

Preference is furthermore given to organic electroluminescent devices, characterised in that they have been produced by a hybrid process in which one or more layers have been applied from solution and one or more other layers have been applied by vapour deposition by means of OVPD or carrier-gas sublimation.

The above-mentioned processes are generally known to the person skilled in the art and can be applied by him without problems to organic electroluminescent devices comprising compounds of the formulae (I) to (XII), as defined above.

An advantageous aspect of the compounds according to the invention is that, owing to the conjugation of the Tr-electrons between the aromatic rings and the alkyne group, a uniform distribution of the frontier orbital electron density is generally present over the entire molecule. This causes very good hole and electron mobilities. However, a limitation should not be derived from this correlation.

Furthermore, good luminescence quantum yields and thus good energy yields can preferably be achieved with the compounds according to the invention.

A further advantageous aspect of the compounds according to the invention is that the ring bridges present in the compounds reduce the number of degrees of rotational freedom of the molecule. This preferably results in a low value of the Stokes shift, which represents a highly desirable property.

The compounds according to the invention furthermore preferably have high thermal stability and a high glass-transition temperature. This has an advantageous effect on the achievable purity of the compounds in the case of purification by means of sublimation methods. In particular for applications at elevated temperature, a high glass-transition temperature effects an extended lifetime of the electronic devices.

Finally, it should be noted that all preferred features and all features not explicitly mentioned as preferred of the above-mentioned compounds according to the invention, the use thereof in electronic devices and the electronic devices themselves can be combined with one another as desired. All resultant combinations are likewise part of this invention.

The following examples are intended to explain the invention in greater detail without restricting it. In particular, the features, properties and advantages described therein of the defined compounds on which the relevant example is based can also be applied to other compounds which are not mentioned in detail, but which fall within the scope of protection of the claims, unless stated otherwise elsewhere.

USE EXAMPLES

Example 1

Synthesis of Compound (1)

The detailed procedure for the synthesis of the di-bridged bromide A can be obtained from the as yet unpublished application DE 102008054141.9.

Trimethylsilylalkyne B

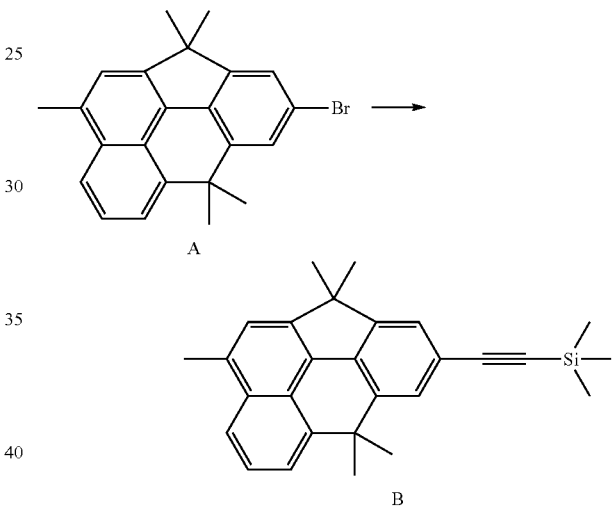

10.0 g (26.5 mmol) of the bromide A are dissolved in 1000 ml of triethylamine, and 11.3 ml (79.5 mmol) of ethynyltrimethylsilane are added. The mixture is degassed by passing in a protective gas, 1.5 g (2.12 mmol) of dichlorobis(triphenylphosphine)palladium(II) and 0.5 g (2.65 mmol) of CuI are added, and the mixture is refluxed for 16 h. The cooled reaction mixture is subsequently carefully added to ice-water, extracted with dichloromethane, dried, evaporated and purified by column chromatography on silica gel, giving 7.9 g (71%) of the product as a yellow oil.

Alkyne C

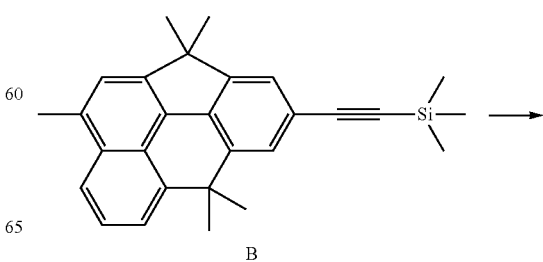

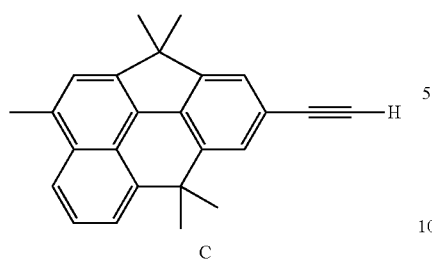

C 7.9 g (18.9 mmol) of B are dissolved in a degassed mixture of 200 ml of water and 200 ml of MeOH, and 6.4 g (68.4 mmol) of KF*2H$_2$O are added in 5 portions at room temperature (RT). The reaction mixture is stirred at RT for 2 h. The reaction solution is diluted with water, extracted with dichloromethane, and the organic phase is dried over MgSO$_4$, evaporated and purified over silica gel with heptane/EA 10:1, giving 3.4 g (10.04 mmol) of the product as a brown oil.

Compound (1)

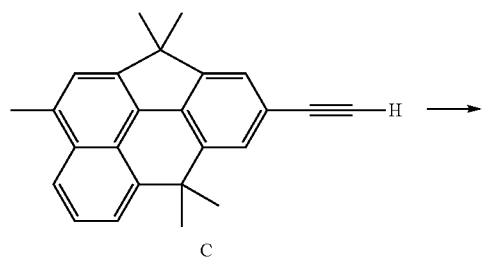

12.0 g (37.23 mmol) of C are dissolved in 81 ml of degassed triethylamine, 4.7 ml (44.7 mmol) of bromobenzene are added, and the mixture is subsequently degassed. 1.02 g of dichlorobis(triphenylphosphine)palladium(II) (1.45 mmol) and 0.55 g of CuI are added to the reaction solution, which is then again briefly degassed. The mixture is subsequently refluxed for 2 h. When the reaction is complete, the reaction solution is added to water, extracted with dichloromethane, and the organic phase is dried over MgSO$_4$. The crude product is crystallised from DMSO and subsequently sublimed, giving 4.2 g (11.1 mmol) of the product as a white solid.

Example 2

Synthesis of Compound (2)

The detailed procedure for the synthesis of the di-bridged bromide D can be obtained from the published application WO 2008/006449.

Compound (2)

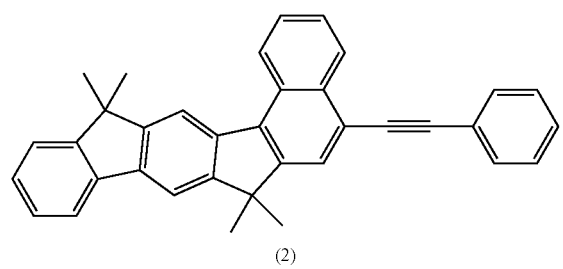

15.3 g (34.8 mmol) of the bromide D are dissolved in 76 ml of triethylamine, and the entire mixture is degassed. 4.97 ml (45.2 mmol) of phenylacetylene, 0.95 g (1.36 mmol) of dichlorobis(triphenylphosphine)palladium(II) and 0.90 g (4.73 mmol) of CuI are subsequently added, and the reaction mixture is again degassed. The mixture is refluxed for 5 h, and, when the reaction is complete, the cooled reaction solution is added to water, extracted with dichloromethane, dried over MgSO$_4$ and evaporated. The product is crystallised from DMSO and subsequently sublimed, giving 9.8 g (21.2 mmol) of the product as a yellowish solid.

Example 3

Synthesis of Compound (3)

The detailed procedure for the synthesis of the di-bridged bromide A can be obtained from the as yet unpublished application DE 102008054141.9.

Compound (3)

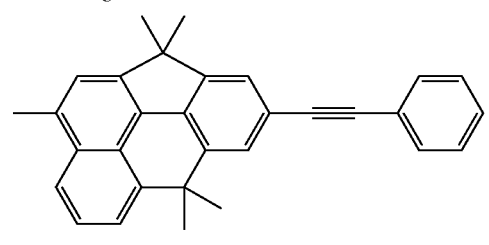

-continued

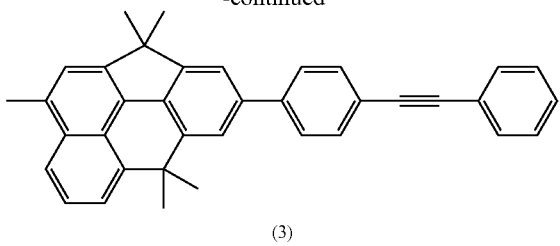

(3)

10.0 g (26.5 mmol) of the bromide A are dissolved in 300 ml of toluene and 150 ml of degassed dioxane, and 132 ml (2 M, 265 mmol) of $Na_2CO_3$ solution are added. 3.25 g (31.8 mmol) of the boronic acid E and 1.53 g (1.32 mmol) of tetrakistriphenylphosphinepalladium are added, and the reaction mixture is subsequently refluxed for 16 h. The cooled reaction mixture is subsequently washed with water, and the organic phase is dried, evaporated and purified by column chromatography on silica gel, giving 6.8 g (55%) of the product as a yellowish solid.

Example 4

Production of OLEDs

OLEDs according to the invention and OLEDs in accordance with the prior art are produced by a general process in accordance with WO 04/058911, which is adapted to the circumstances described here (layer-thickness variation, materials used).

The results for various OLEDs are presented in Device Examples a to e below (see Table 1). Glass plates coated with structured ITO (indium tin oxide) having a thickness of 150 nm are coated with 20 nm of PEDOT (poly(3,4-ethylene-dioxy-2,5-thiophene, purchased from H. C. Starck, Goslar, Germany, spin-coated from water) for improved processing. These coated glass plates form the substrates to which the OLEDs are applied. The OLEDs have in principle the following layer structure: substrate/optional hole-injection layer (HIL1) 5 nm/hole-transport layer (HTL) 140 nm/electron-blocking layer (EBL) 20 nm/emission layer (EML) 30 nm/optional hole-blocking layer (HBL) 10 nm/electron-transport layer (ETL) 20 nm and finally a cathode. The cathode is formed by an aluminium layer with a thickness of 100 nm, where, depending on the electron-transport material used, an electron-injection layer (EIL) comprising LiF or LiQ with a thickness of 1 nm is introduced between the cathode and the electron-transport layer. The materials used for the production of the OLEDs are shown in Table 2.

All materials are applied by thermal vapour deposition in a vacuum chamber. The emission layer here always consists of at least one matrix material (host material) and an emitter (dopant), which is admixed with the matrix material or materials in a certain proportion by volume by co-evaporation. An expression such as H1: (1) (95%:5%) here means that material H1 is present in the layer in a proportion by volume of 95% and compound (1) is present in the layer in a proportion of 5%.

The OLEDs are characterised by standard methods. For this purpose, the electroluminescence spectra, the current efficiency (measured in cd/A), the power efficiency (measured in lm/W) and the external quantum efficiency (EQE, measured in per cent) as a function of the luminance, calculated from current/voltage/luminance characteristic lines (IUL characteristic lines), and the lifetime are determined. The lifetime is defined as the time after which the luminance has dropped to half from a certain initial luminance. This value can be converted to a figure for other initial luminances with the aid of conversion formulae known to the person skilled in the art. The lifetime for an initial luminance of 1000 $cd/m^2$ is the usual figure here.

Examples a to c in Table 1 represent electroluminescent devices according to the invention which comprise a compound of the formula (I) as dopant in an emitting layer. Examples e and f represent comparative examples, in which the compounds of the prior art CD1 and CD2 are used.

The examples show (cf. Table 1) that significantly better performance data for the electroluminescent device, such as an improved lifetime and improved energy efficiency, are obtained with the compounds according to the invention.

TABLE 1

| | HTL Thickness | EBL | EML | ETL/EIL | Voltage for 1000 $cd/m^2$ | Efficiency at 1000 $cd/m^2$ | Efficiency at 1000 $cd/m^2$ | EQE at 1000 $cd/m^2$ | CIE x/y at 1000 $cd/m^2$ | $LT_{50}$ [h] @ 1000 cd/A |
|---|---|---|---|---|---|---|---|---|---|---|
| Ex. | | | | | | | | | | |
| a | HTM1 140 nm | NPB | H1:(1) (95%:5%) | $Alq_3$/LiF 1 nm | 5.6 V | 5.1 cd/A | 3.8 lm/W | 5.0 | 0.148/0.114 | 2110 |
| b | HTM1 140 nm | NPB | H1:(2) (95%:5%) | $Alq_3$/LiF 1 nm | 5.7 V | 5.0 cd/A | 3.8 lm/W | 4.9 | 0.147/0.151 | 2150 |
| c | HTM1 140 nm | NPB | H1:(3) (95%:5%) | $Alq_3$/LiF 1 nm | 5.5 V | 5.2 cd/A | 3.9 lm/W | 5.1 | 0.146/0.113 | 2250 |
| Comp. | | | | | | | | | | |
| d | HTM1 140 nm | NPB | H1:CD1 (95%:5%) | $Alq_3$/LiF 1 nm | 8.1 V | 3.5 cd/A | 2.7 lm/W | 3.4 | 0.151/0.123 | 1070 |
| e | HTM1 140 nm | NPB | H1:CD2 (95%:5%) | $Alq_3$/LiF 1 nm | 8.3 V | 3.4 cd/A | 2.6 lm/W | 3.3 | 0.151/0.152 | 980 |

TABLE 2
Structural formulae of the materials used
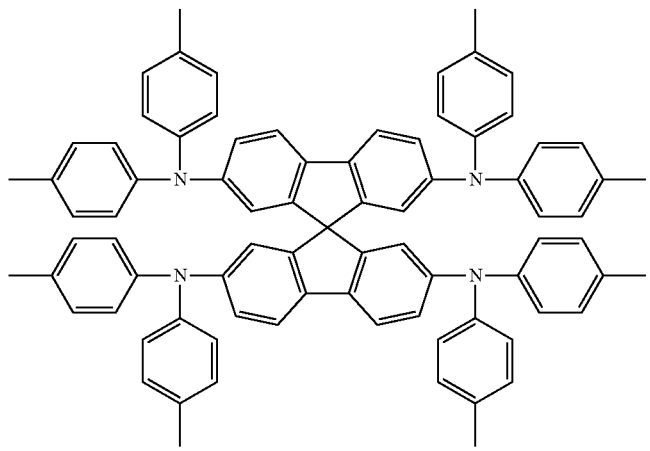
HTM1
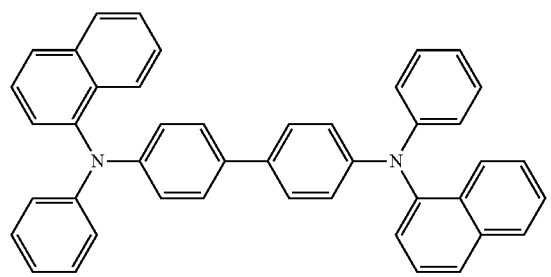 [SMILES: c1ccc(N(c2ccc(-c3ccc(N(c4ccccc4)c4cccc5ccccc45)cc3)cc2)c2cccc3ccccc23)cc1]
NPB
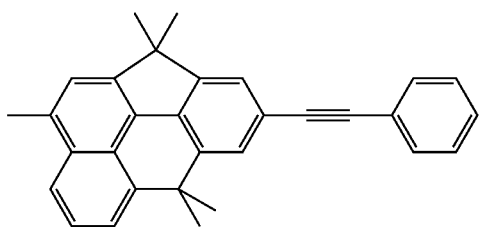 [SMILES: Cc1cc2c3c4c(cccc14)C(C)(C)c1cc(C#Cc4ccccc4)cc(c1-3)C2(C)C]
(1)
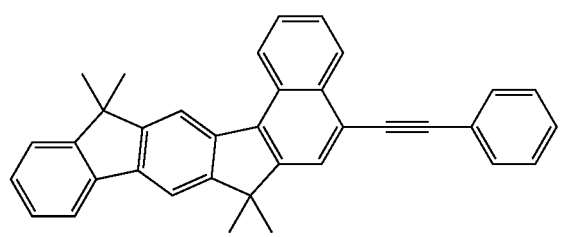 [SMILES: CC1(C)c2ccccc2-c2cc3c(cc21)-c1c(cc(C#Cc2ccccc2)c2ccccc12)C3(C)C]
(2)

TABLE 2-continued
Structural formulae of the materials used
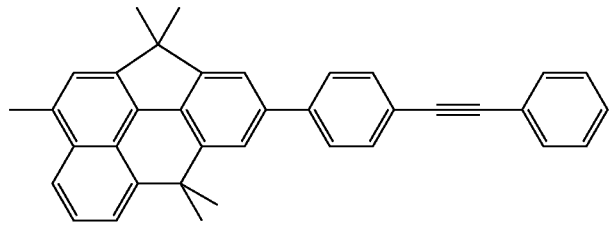 [SMILES: Cc1cc2c3c4c(cccc14)C(C)(C)c1cc(-c4ccc(C#Cc5ccccc5)cc4)cc(c1-3)C2(C)C]
(3)
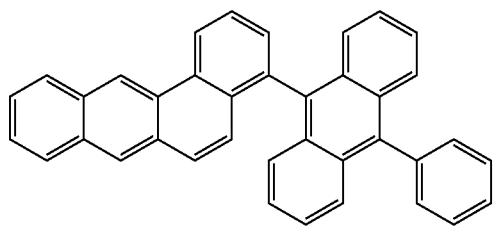 [SMILES: c1ccc(-c2c3ccccc3c(-c3cccc4c3ccc3cc5ccccc5cc34)c3ccccc23)cc1]
H1
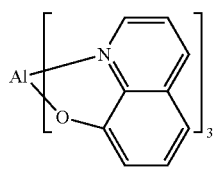
Alq₃
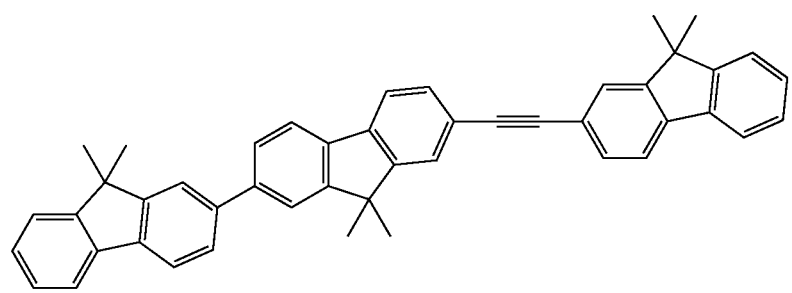 [SMILES: CC1(C)c2ccccc2-c2ccc(C#Cc3ccc4c(c3)C(C)(C)c3cc(-c5ccc6c(c5)C(C)(C)c5ccccc5-6)ccc3-4)cc21]
CD1
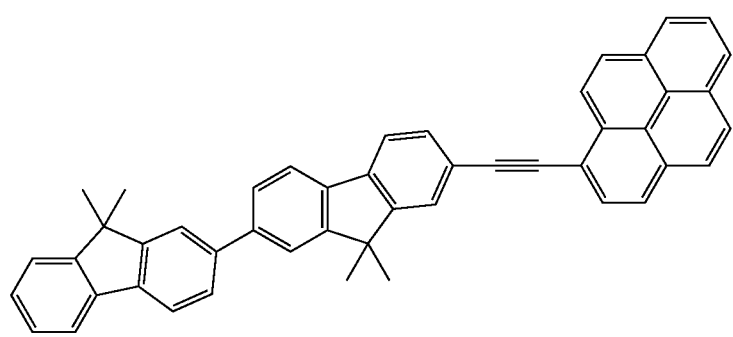 [SMILES: CC1(C)c2ccccc2-c2ccc(-c3ccc4c(c3)C(C)(C)c3cc(C#Cc5ccc6ccc7cccc8ccc5c6c78)ccc3-4)cc21]
CD2

The invention claimed is:
1. A compound of formulae (IV), (V), or (VI)

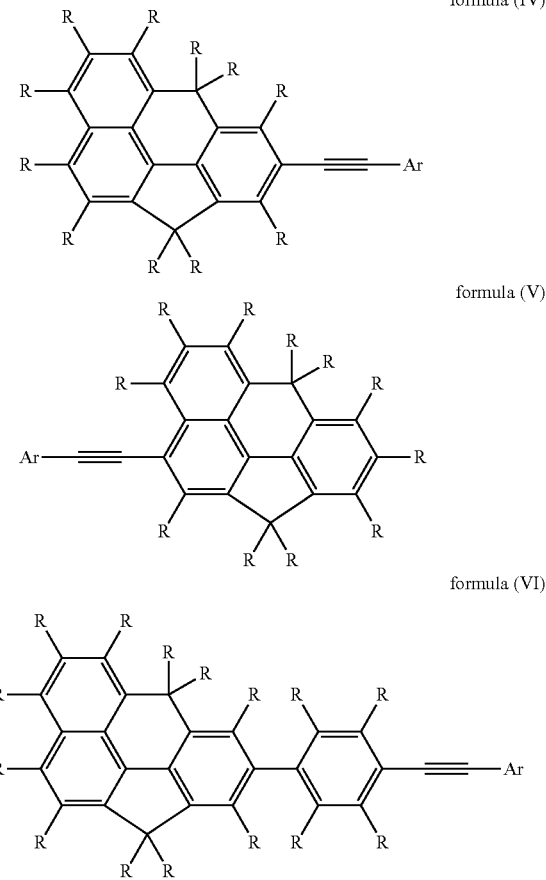

wherein
R is on each occurrence, identically or differently, H, D, F, Cl, Br, I, $N(R^1)_2$, CN, $NO_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy or thioalkoxy group having 1 to 40 C atoms or an alkenyl group having 2 to 40 C atoms or a branched or cyclic alkyl, alkoxy or thioalkoxy group having 3 to 40 C atoms, where the said groups may each be substituted by one or more radicals $R^1$ and where one or more adjacent or non-adjacent $CH_2$ groups may be replaced by $R^1C=CR^1$, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S, COO or $CONR^1$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may be substituted by one or more radicals $R^1$, or an aralkyl or heteroaralkyl group having 5 to 60 aromatic ring atoms, which may in each case be substituted by one or more radicals $R^1$; two or more substituents R on the phenylene groups and/or on the naphthylene groups and/or on the substituents Ar here may be linked to one another and optionally form a mono- or polycyclic aliphatic or aromatic ring system;
$R^1$ is on each occurrence, identically or differently, H, D, F, Cl, Br, I, CN or an aliphatic, aromatic or heteroaromatic organic radical having 1 to 40 C atoms, in which, in addition, one or more H atoms may be replaced by D, F, Cl, Br, I, CN, $OR^2$, $SR^2$ or $N(R^2)_2$, where one or more adjacent or non-adjacent $CH_2$ groups may be replaced by $R^2C=CR^2$, COO or $CONR^2$; two or more adjacent or non-adjacent radicals $R^1$ here may be linked to one another and optionally form a mono- or polycyclic, aliphatic or aromatic ring system;
$R^2$ is on each occurrence, identically or differently, H, D or an aliphatic, aromatic or heteroaromatic organic radical having 1 to 20 C atoms, in which, in addition, one or more H atoms may be replaced by D or F; two or more adjacent or non-adjacent radicals $R^2$ here may be linked to one another and optionally form a mono- or polycyclic aliphatic or aromatic ring system; and
Ar is on each occurrence, identically or differently, an aromatic or heteroaromatic ring system having 5 to 60 aromatic ring atoms, which is optionally substituted by one or more radicals R.

2. The compound of claim 1, wherein R is H, D, CN or a straight-chain alkyl group having 1 to 20 C atoms or an alkenyl group having 2 to 20 C atoms or a branched or cyclic alkyl group having 3 to 20 C atoms or an aromatic or heteroaromatic ring system having 5 to 40 aromatic ring atoms, where the said groups are optionally substituted by one or more identical or different radicals $R^1$.

3. A process for preparing a compound of claim 1, said process comprising a synthetic sequence including at least one coupling reaction between an aryl group and an alkynyl group.

4. An oligomer, polymer, or dendrimer comprising one or more identical or different compounds of claim 1, where a bond to a radical R in said compounds is replaced by the bond to the adjacent recurring unit.

5. A formulation comprising at least one compound of claim 1 and at least one solvent.

6. A formulation comprising at least one oligomer, polymer, or dendrimer, of claim 4 and at least one solvent.

7. An electronic device comprising the compound of claim 1.

8. An electronic device comprising the oligomer, polymer, or dendrimer, of claim 4.

9. The electronic device of claim 8, wherein said electronic device is selected from the group consisting of organic electroluminescent devices, organic field-effect transistors, organic thin-film transistors, organic light-emitting transistors, organic integrated circuits, organic solar cells, organic field-quench devices, light-emitting electrochemical cells, organic laser diodes, and organic photoreceptors.

10. The electronic device of claim 7, wherein said electronic device is an organic electroluminescent device, wherein said compound is employed as matrix material for fluorescent dopants or phosphorescent compounds or as emitting material (dopant), as hole-transport material, as hole-injection material or as electron-transport material.

11. The electronic device of claim 7, wherein said electronic device is selected from the group consisting of organic electroluminescent devices, organic field-effect transistors, organic thin-film transistors, organic light-emitting transistors, organic integrated circuits, organic solar cells, organic field-quench devices, light-emitting electrochemical cells, organic laser diodes, and organic photoreceptors.

* * * * *